US012397017B2

(12) United States Patent
Reed

(10) Patent No.: US 12,397,017 B2
(45) Date of Patent: *Aug. 26, 2025

(54) FORTIFIED NUTRITIONAL LUBRICATING DROPS FOR DRY EYE DISEASE

(71) Applicant: Platform Ophthalmic Innovations, LLC, Brentwood, TN (US)

(72) Inventor: Kenneth Reed, Brentwood, TN (US)

(73) Assignee: PLATFORM OPHTHALMIC INNOVATIONS, LLC, Brentwood, TN (US)

( * ) Notice: Subject to any disclaimer, the term of this patent is extended or adjusted under 35 U.S.C. 154(b) by 55 days.

This patent is subject to a terminal disclaimer.

(21) Appl. No.: 17/986,092

(22) Filed: Nov. 14, 2022

(65) Prior Publication Data

US 2024/0156859 A1 May 16, 2024

Related U.S. Application Data

(63) Continuation-in-part of application No. 17/574,288, filed on Jan. 12, 2022, now Pat. No. 11,951,123.

(51) Int. Cl.

| A61K 31/79 | (2006.01) |
|---|---|
| A61K 9/00 | (2006.01) |
| A61K 31/198 | (2006.01) |
| A61K 31/728 | (2006.01) |
| A61K 47/02 | (2006.01) |
| A61K 47/12 | (2006.01) |
| A61K 47/18 | (2017.01) |
| A61K 47/22 | (2006.01) |
| A61K 47/26 | (2006.01) |
| A61K 47/32 | (2006.01) |
| A61K 47/44 | (2017.01) |

(52) U.S. Cl.
CPC ............ *A61K 31/79* (2013.01); *A61K 9/0048* (2013.01); *A61K 31/198* (2013.01); *A61K 31/728* (2013.01); *A61K 47/02* (2013.01); *A61K 47/12* (2013.01); *A61K 47/18* (2013.01); *A61K 47/22* (2013.01); *A61K 47/26* (2013.01); *A61K 47/32* (2013.01); *A61K 47/44* (2013.01)

(58) Field of Classification Search
CPC .... A61K 31/79; A61K 9/0048; A61K 31/198; A61K 31/728; A61K 47/12; A61K 47/18; A61K 47/22; A61K 47/27; A61K 47/32; A61K 47/44

See application file for complete search history.

(56) References Cited

U.S. PATENT DOCUMENTS

| 5,981,607 | A | 11/1999 | Ding et al. |
|---|---|---|---|
| 7,638,142 | B2 | 12/2009 | Krawitz |
| 8,957,048 | B2 | 2/2015 | Vehige et al. |
| 8,957,110 | B2 | 2/2015 | Aleo et al. |
| 9,161,905 | B2 | 10/2015 | Korb et al. |
| 9,480,645 | B2 | 11/2016 | Yu |
| 9,668,996 | B2 | 6/2017 | O'Haimhirgin |
| 10,279,005 | B2 | 5/2019 | Gore et al. |
| 10,383,889 | B2 | 8/2019 | Belmonte et al. |
| 10,660,848 | B2 | 5/2020 | Torres et al. |
| 2006/0251685 | A1 | 11/2006 | Yu et al. |
| 2008/0050335 | A1 | 2/2008 | Faour et al. |
| 2017/0105934 | A1* | 4/2017 | Mizutare ................. A61K 47/12 |
| 2023/0144779 | A1* | 5/2023 | Singh Rawat ......... A61K 47/10 514/233.5 |

FOREIGN PATENT DOCUMENTS

WO WO-2017182138 A1 * 10/2017 ......... A61K 31/5377

OTHER PUBLICATIONS

Aragona P, Rania L, Micali A, Puzzolo D. Nutrition and dry eye. Current Ophthalmology Reports. Jun. 2013;1(2):58-64.
Aragona P, Rania L, Roszkowska AM, Spinella R, Postorino E, Puzzolo D, Micali A. Effects of amino acids enriched tears substitutes on the cornea of patients with dysfunctional tear syndrome. Acta ophthalmologica. Sep. 2013;91(6):e437-44).
Bartollino S, Palazzo M, Semeraro F, Parolini B, Caruso C, Merolla F, Guerra G, Costagliola C. Effects of an antioxidant protective topical formulation on retinal tissue of UV-exposed rabbits. International ophthalmology. Jan. 2020 8:1-9.
Baudouin C, Aragona P, Messmer EM, Tomlinson A, Calonge M, Boboridis KG, Akova YA, Geerling G, Labetoulle M, Rolando M. Role of hyperosmolarity in the pathogenesis and management of dry eye disease: proceedings of the Ocean group meeting. The ocular surface. Oct. 1, 2013;11(4):246-58.
Brocker C, Thompson DC, Vasiliou V. The role of hyperosmotic stress in inflammation and disease. Biomolecular concepts. Aug. 1, 2012;3(4):345-64.

(Continued)

*Primary Examiner* — Zohreh A Fay
(74) *Attorney, Agent, or Firm* — Elizabeth M. Crompton; Parker Poe Adams & Bernstein, LLP

(57) ABSTRACT

The invention describes ophthalmic pharmaceutical formulations comprising pharmaceutical ingredients to address DED symptoms. In one aspect of the invention, an ophthalmic pharmaceutical formulation comprises: 1) lubricity-promoting ingredient(s) such as those listed in the FDA over the counter (OTC) monograph for ophthalmics as demulcents and 2) surfactant(s) that solubilize lipids, assist in lubrication, and assist in easily spreading over hydrophobic surfaces; and/or 3) lipid and/or oil ingredient(s) that assist in film formation and the spreading of tear fluid while promoting (or at least not inhibiting) lubrication; and/or 4) mucoadhesive and viscosity promoting polymer(s) that demonstrate shear thinning flow behavior. The pharmaceutical ingredients and osmoprotectant/tonicity ingredients are combined with ingredients that provide direct to the eye nutritional support that is comprehensive in nature. The total nutritional approach uses metabolically important tear fluid amino acids, vitamins, natural antioxidants such as ferulic acid, and both fatty acids/triglycerides and sugar molecules as energy sources. The invention results in both improved eye health and improved dry eye patient comfort.

20 Claims, No Drawings

(56) References Cited

OTHER PUBLICATIONS

Butovich IA, Lipidomics of human meibomian gland secretions: chemistry, biophysics, and physiological role of meibomian lipids. Progress in lipid research. Jul. 1, 2011;50(3):278-301.

Butovich IA, Meibomian glands, meibum, and meibogenesis. Experimental eye research. Oct. 1, 2017;163:2-16.

Calder PC, Jensen GL, Koletzko BV, Singer P, Wanten GJ. Lipid emulsions in parenteral nutrition of intensive care patients: current thinking and future directions. Intensive care medicine. May 2010;36(5):735-49.

Chen W, Zhang X, Li J, Wang Y, Chen Q, Hou C, Garrett Q. Efficacy of osmoprotectants on prevention and treatment of murine dry eye. Investigative ophthalmology & visual science. 2013.

Gilbard JP. Dry eye and the role of nutrition. Optom Today. Jun. 2004:34-41.

Jimenez-Arias D, Garcia-Machado FJ, Morales-Sierra S, Garcia-Garcia AL, Herrera AJ, Valdes F, Luis JC, Borges AA. A Beginner's Guide to Osmoprotection by Biostimulants. Plants. Feb. 2021;10(2):363.

Larmo P, Järvinen R, Laihia J, Loyttyniemi E, Maavirta L, Yang B, Kallio H, Sandberg-Lall M. Effects of a sea buckthorn oil spray emulsion on dry eye. Contact Lens and Anterior Eye. Aug. 1, 2019;42(4):428-33.

Modugno RL, Feuerman OM, La Gloria Valerio A, Scalora T, Salami E. A Novel Liposome-Based, Aminoacid-and Vitamin-Containing Tear Substitute in Patients with Evaporative Dry Eye Disease. A Pilot Prospective Study. J Comm Med and Pub Health Rep. 2021;2(2).

O'Neil EC, Henderson M, Massaro-Giordano M, Bunya VY. Advances in Dry Eye Disease Treatment. Curr Opin Ophthalmol. May 2019;30(3):166-78.

Perminaite K, Marksa M, Ivanauskas L, Ramanauskiene K. Preparation of Ophthalmic Microemulsions Containing Lithuanian Royal Jelly and Their Biopharmaceutical Evaluation. Processes. Apr. 2021;9(4):616.

Pucker AD, Ng SM, Nichols JJ. Over the counter (OTC) artificial tear drops for dry eye syndrome. Cochrane Database of Systematic Reviews. 2016(2).

Rashid S, Jin Y, Ecoiffier T, Barabino S, Schaumberg DA, Dana MR. Topical omega-3 and omega-6 fatty acids for treatment of dry eye. Archives of ophthalmology. Feb. 1, 2008;126(2):219-25.

Salehi B, Quispe C, Sharifi-Rad J, Cruz-Martins N, Nigam M, Mishra AP, Konovalov DA, Orobinskaya V, Abu-Reidah IM, Zam W, Sharopov F. Phytosterols: from preclinical evidence to potential clinical applications. Frontiers in Pharmacology. Jan. 14, 2021;11:1819.

Vizzarri FR, Palazzo MA, Bartollino SI, Casamassima DO, Parolini BA, Troiano PA, Caruso CI, Costagliola CI. Effects of an antioxidant protective topical formulation on eye exposed to ultraviolet-irradiation: a study in rabbit animal model. Physiological research. May 1, 2018;67(3):457-64.

Worthley LI, Atkinson M. Nutrition in the critically ill patient: part II. Parenteral nutrition.

Widjaja-Adhi MA, Silvaroli JA, Chelstowska S, Trischman T, Bederman I, Sayegh R, Golczak M. Deficiency in Acyl-CoA: Wax Alcohol Acyltransferase 2 causes evaporative dry eye disease by abolishing biosynthesis of wax esters. The FASEB Journal. Oct. 2020;34(10):13792-808.

Yao L, Hammond EG. Isolation and melting properties of branched-chain esters from lanolin. Journal of the American Oil Chemists' Society. Jun. 2006;83(6):547-52.

Zakaria El-Sayed HE, Mowafi S, El-Kheir A, El-Khatib EM. A Comprehensive Critique on Wool Grease Extraction, Properties and Applications. Egyptian Journal of Chemistry. Dec. 1, 2018;61(6):1151-9.

Gaia Favero, Enrico Moretti, Kristina Krajcikova, Vladimíra Tomeckova, Rita Rezzani. Evidence of Polyphenols Efficacy against Dry Eye Disease. Antioxidants 2021, 10, 190.

Kamila Zduńska Agnieszka Dana Anna Kolodziejczak Helena Rotsztejn. Antioxidant Properties of Ferulic Acid and Its Possible Application. Skin Pharmacol Physiol 2018;31:332-336.

Fu-Hsiung Lin, Jing-Yi Lin, Ravindra D. Gupta, Joshua A. Tournas, James A. Burch, M. Angelica Selim, Nancy A. Monteiro-Riviere, James M. Grichnik, Jan Zielinski, Sheldon R. Pinnell. Ferulic Acid Stabilizes a Solution of Vitamins C and E and Doubles its Photoprotection of Skin. J Invest Dermatol 125:826-832, 2005.

Shigeru Nakamura, Yuki Kimura, Daisuke Mori, Toshihiro Imada, Yusuke Izuta, Michiko Shibuya, Hisayo Sakaguchi, Erina Oonishi, Naoko Okada, Kenji Matsumoto, Kazuo Tsubota. Restoration of Tear Secretion in a Murine Dry Eye Model by Oral Administration of Palmitoleic Acid. Nutrients 2017, 9, 364; doi:10.3390/nu9040364.

Provinal Technical Data Sheet EE-2021.

* cited by examiner

FORTIFIED NUTRITIONAL LUBRICATING DROPS FOR DRY EYE DISEASE

CROSS-REFERENCE TO RELATED APPLICATION

This application is a continuation-in-part of U.S. patent application Ser. No. 17/574,288, filed on Jan. 12, 2022, which is incorporated by reference in its entirety.

FIELD OF THE INVENTION

The present invention relates to ophthalmic compositions that are useful in promoting general corneal health and in the treatment and/or prevention of dry eye or keratoconjunctivitis in a human or other mammal. Compositions are disclosed which include an active ingredient and surfactants, and/or oil(s) (oil-in-water emulsions), and/or mucoadhesive polymers, and/or metabolically important amino acids, and/or vitamins (natural antioxidants), and/or energy source(s) that are helpful as artificial tears and therapeutic agent delivery solutions.

BACKGROUND OF THE INVENTION

The condition of dry eye disease (DED) (also called dry eye syndrome) is commonly considered to result from dehydration of the tear film layer (insufficient amount of tear fluid) and/or tear producing glands not functioning correctly (poor quality of tear fluid). This results in patient discomfort that ranges in severity. DED is often referred to as having a dry eye. It is rare that DED causes permanent vision loss, but a condition of severe dry eye is painful and difficult to endure, especially if chronic. There is a need for drug products that are useful for treating DED. Disadvantages of available prescription products include high cost, mixed efficacy, a delay in benefit, and ocular burning that causes patient discomfort.

SUMMARY OF THE INVENTION

Aspects and advantages of the invention will be set forth in part in the following description, or may be obvious from the description, or may be learned through practice of the invention.

This invention provides ophthalmic pharmaceutical formulations that enhance ocular health while simultaneously improving eye comfort. In one aspect of the invention, an ophthalmic pharmaceutical formulation comprises: 1) lubricity-promoting ingredient(s) such as those listed in the FDA over the counter (OTC) monograph for ophthalmics as demulcents; 2) surfactant(s) that solubilize oil(s) and/or Ascorbyl Palmitate and/or Vitamin D and/or Vitamin E, assist in lubrication, and assist in easily spreading over hydrophobic surfaces; and/or oil(s) that assist in film formation and the spreading of tear fluid while promoting (or at least not inhibiting) lubrication; and/or 4) mucoadhesive polymer(s) that demonstrate shear thinning flow behavior; and/or 5) osmoprotectants. In some embodiments, the same ingredient can provide the effects of one or more of the lubricity-promoting ingredient(s), surfactant(s), lipid and/or oil(s), and/or mucoadhesive polymer(s). In another aspect of the invention, the ophthalmic pharmaceutical formulation provides benefits to a patient including one or more of the following: less blurring in vision, a reduction in the feelings of abrasion during blinks, and general improvements in dry eye patient comfort.

In some embodiments, the ophthalmic pharmaceutical formulations provide for the nutritional needs of corneal epithelial cells in the same manner as a total parenteral nutrition approach. Nutritional supplementation is made possible with amino acids that are selected for their metabolic importance and osmoprotection. Sugars such as dextrose, mannitol, and sorbitol, and fatty acids and/or triglycerides may be provided as energy sources for corneal cells. Corneal antioxidant protectants that include Vitamin C and/or Ascorbyl Palmitate and/or Vitamin D and/or Vitamin E may be used. Natural antioxidants such as Ferulic acid may protect both formulation ingredients (e.g., Vitamin C) and corneal cells from oxidation. Oils may be added to provide nutritional (energy) needs, and/or antioxidant protection and/or anti-inflammatory activity. Sugar alcohols such as Sorbitol and Mannitol and carbohydrates such as Trehalose may be provided as osmoprotectants.

In another embodiment, the ophthalmic pharmaceutical formulations may be utilized as platform ophthalmic drug delivery systems. That is, the formulations can act as vehicles for various agents that demonstrate ocular pharmacological action.

In some embodiments, the ophthalmic pharmaceutical formulations are in the form of a microemulsion or nanoemulsion formed from lipid(s) and/or natural oil(s) and surfactants which may improve administration of lipophilic pharmacologic agents that have poor water solubility.

In an embodiment, the ophthalmic pharmaceutical formulations disclosed herein may be administered to a patient in a method for treating DED. In another embodiment, the ophthalmic pharmaceutical formulations disclosed herein may be combined with an effective amount of an ophthalmic active ingredient and administered to a patient in a method for treating an ophthalmic condition.

These and other features, aspects and advantages of the present invention will become better understood with reference to the following description and appended claims.

DETAILED DESCRIPTION OF THE INVENTION

The cornea of the eye is highly innervated, and any pain or irritation is very uncomfortable. The corneal epithelium is the outermost layer of cells and must be kept moist with the tear fluid. The tear fluid in the eye is a combination of 1) water, 2) mucus, and 3) lipids/amphiphiles. The water portion maintains eye cell hydration and possesses nutrients for cornea cells. The mucus helps to maintain cell hydration, provides lubrication during eye blinks, and assists in ensuring that tear fluid is spread evenly over the eye. The shear thinning properties of mucus ensure that tear fluid is spread evenly over the eye without the uncomfortable patient perception that the eyelid is "dragging" or "sticky". Tear lipids and amphiphiles provide lubrication during eye blinks and assist in ensuring that tear fluid is spread evenly over the eye. The lipid film layer must be transparent and demonstrate transient stability in between eye blinks.

One embodiment of the invention relates to ophthalmic pharmaceutical formulations comprising one or more of the following: 1) lubricity-promoting ingredient(s), 2) surfactant(s), and/or 3) lipid and/or oil(s), and/or 4) mucoadhesive polymer(s). In some embodiments, the same ingredient can provide the effects of one or more of the lubricity-promoting ingredient(s), surfactant(s), lipid(s), and/or mucoadhesive polymer(s). In another embodiment of the invention, the ophthalmic pharmaceutical formulations further comprise one or more ingredients for nutritional supplementation. In another embodiment of the invention, the ophthalmic pharmaceutical formulations further comprise one or more ingredients for hyperosmotic protection. In yet another embodiment, the ophthalmic pharmaceutical formulations comprise a pharmacologically active ingredient useful for treating ocular conditions. In additional embodiments, the ophthalmic pharmaceutical formulations comprise tonicity agents and/or osmoprotectants that may also function as antioxidants, sources of amino acid(s), and/or energy sources. The same ingredient may provide multiple functions in the ophthalmic pharmaceutical formulations described herein.

In some embodiments, an advantage of the ophthalmic pharmaceutical formulations is that they have sufficient light transparency to produce less visual blurring for the patient. In an embodiment, the ophthalmic pharmaceutical formulations are formulated as microemulsions or as nanoemulsions. Oil in water emulsions are dispersions whereby discrete oil droplets are surrounded by water. Oil and water normally separate into separate phases. However, surfactants can be used to stabilize the dispersed oil droplet. The oil droplets in microemulsions or nanoemulsions are sufficiently small so as to maximize light transmission. This results in less blurred vision than that noted with petrolatum ointments or emulsions that have a milk-like appearance. In addition, the eye is exposed to water and a small amount of oil. Thus, a favorable aqueous eye environment is maintained. The oils not only assist in protecting the eye but can also be used as a means to solubilize water insoluble drug molecules that are lipophilic in nature. It is of benefit to the practice of ophthalmology that numerous active molecules can be solubilized that are then more effectively used in the treatment of ocular inflammation, ocular pain, glaucoma, ocular infections and other ocular ailments. Active agents that may be included in the ophthalmic pharmaceutical formulations of the invention include, but are not limited to: Diclofenac, Pranoprofen, Bimatoprost, and Prednisolone.

In an embodiment, lubricity-promoting ingredients as used herein are referred to in the FDA OTC (over the counter) monograph for dry eye products, 21 CFR 349, as demulcents. In the cited monograph, a demulcent is defined as "an agent, usually a water-soluble polymer, which is supplied topically to the eye to protect and lubricate mucous membrane surfaces and relieve dryness and irritation." A demulcent is a soothing, usually mucilaginous substance that is used to relieve pain in inflamed or irritated mucous membranes. OTC dry eye demulcents are also considered to be lubricating agents and may be polymers such as povidone or carboxymethylcellulose. As used herein, the terms lubricity promoting ingredient and demulcent are used interchangeably. Demulcents that can be used in the ophthalmic pharmaceutical formulations of the invention include but are not limited to povidone (polyvinyl pyrrolidone or PVP) and polyethylene glycol (PEG), such as polyethylene glycol 400 (PEG 400). Other demulcents that can be used in the ophthalmic pharmaceutical formulations of the invention include the demulcents listed in the FDA's OTC monograph. In an embodiment, the present invention includes ophthalmic pharmaceutical compositions comprising one or more of the following demulcents: carboxymethylcellulose sodium, hydroxyethyl cellulose, hypromellose, methylcellulose, dextran 70, gelatin, glycerin, polyethylene glycol 300, polyethylene glycol 400, polysorbate 80, propylene glycol, polyvinyl alcohol, and povidone.

The amount of demulcent to be included in the ophthalmic pharmaceutical formulations of the invention is an amount that is sufficient to provide lubricity to the formulation and/or to lubricate the surface of the eye. In some embodiments, the ophthalmic pharmaceutical formulations may comprise up to about 5% (w/w), or up to about 8% (w/w) demulcent or combination of demulcents. In some embodiments, the ophthalmic pharmaceutical formulations may comprise about 0.1% to about 8% (w/w), or about 0.5% (w/w) to about 5% (w/w), or about 1% (w/w) to about 3% (w/w) demulcent or combination of demulcents. In still other embodiments, the ophthalmic pharmaceutical formulations may comprise a demulcent in an amount selected from the group consisting of about 0.1% (w/w), about 0.2% (w/w), about 0.3% (w/w), about 0.4% (w/w), about 0.5% (w/w), about 0.6% (w/w), about 0.7% (w/w), about 0.8% (w/w), about 0.9% (w/w), about 1.0% (w/w), about 1.1% (w/w), about 1.2% (w/w), about 1.3% (w/w), about 1.4% (w/w), about 1.5% (w/w), about 1.6% (w/w), about 1.7% (w/w), about 1.8% (w/w), about 1.9% (w/w), about 2.0% (w/w), about 2.1% (w/w), about 2.2% (w/w), about 2.3% (w/w), about 2.4% (w/w), about 2.5% (w/w), about 2.6% (w/w), about 2.7% (w/w), about 2.8% (w/w), about 2.9% (w/w), and about 3.0% (w/w). In various embodiments, demulcent concentrations include, but are not limited to the following: Carboxymethylcellulose sodium (about 0.1 to about 5% (w/w)), Hydroxyethyl cellulose (about 0.1 to about 5% (w/w)), Hypromellose (about 0.1 to about 5% (w/w)), Methylcellulose (about 0.1 to about 5% (w/w)), Dextran 70 (about 0.1 to about 2.5% (w/w)), Gelatin (about 0.05 to about 2.5% (w/w)), Glycerin (about 0.1 to about 2% (w/w)), Polyethylene glycol 300 (about 0.1 to about 2% (w/w)), Polyethylene glycol 400 (about 0.1 to about 2% (w/w)), Polysorbate 80 (about 0.1 to about 6% (w/w)), propylene glycol (about 0.1 to about 5% (w/w)), Polyvinyl alcohol (about 0.1 to about 5% (w/w)), and Povidone (about 0.05 to about 5% (w/w)).

A surfactant is defined as a molecule that possesses both a hydrophilic portion and a lipophilic portion of the same molecule. Surfactants are often used to stabilize (prevent phase separation) of oil (lipid) in water emulsions. Emulsions in this application are oil (lipids) droplets dispersed in water. Emulsions include microemulsions and nanoemulsions, which comprise droplets that are small enough in size to allow visual transparency. Surfactants also lower the surface tension of water and assist in ensuring that tear fluid is spread evenly over the eye. In an embodiment, the present invention includes ophthalmic pharmaceutical compositions comprising one or more of the following surfactants: polysorbate 80, tyloxapol, polyoxyl 35 castor oil (cremophor EL), nonoxynol-9, polyoxyl 40 hydrogenated castor oil (cremophor RH), polyoxyl 15 hydroxystearate, polysorbate 20, octoxynol-40, poloxamer 407, poloxamer 188, carbomer copolymer type A, and carbomer copolymer type B.

The amount of surfactant to be included in the ophthalmic pharmaceutical formulations of the invention is an amount that is sufficient to form and stabilize any microemulsion in the ophthalmic pharmaceutical formulation. In some embodiments, the ophthalmic pharmaceutical formulations may comprise up to about 8% (w/w) surfactant or combination of surfactants. In some embodiments, the ophthalmic pharmaceutical formulations may comprise about 0.005% (w/w) to about 35% (w/w) surfactant or combination of surfactants. In still other embodiments, the ophthalmic pharmaceutical formulations may comprise one or more surfactants in an amount selected from the group consisting of about 0.005% (w/w), about 0.006% (w/w), about 0.007% (w/w), about 0.008% (w/w), about 0.009% (w/w), about 0.01% (w/w), about 0.011% (w/w), about 0.012% (w/w), about 0.013% (w/w), about 0.014% (w/w), about 0.015% (w/w), about 0.016% (w/w), about 0.017% (w/w), about 0.018% (w/w), about 0.019% (w/w), about 0.02% (w/w), about 0.021% (w/w), about 0.022% (w/w), about 0.023% (w/w), about 0.024% (w/w), about 0.025% (w/w), about 0.026% (w/w), about 0.027% (w/w), about 0.028% (w/w), about 0.029% (w/w), about 0.03% (w/w), about 0.031% (w/w), about 0.032% (w/w), about 0.033% (w/w), about 0.034% (w/w), about 0.035% (w/w), about 0.036% (w/w), about 0.037% (w/w), about 0.038% (w/w), about 0.039% (w/w), about 0.04% (w/w), about 0.041% (w/w), about 0.042% (w/w), about 0.043% (w/w), about 0.044% (w/w), about 0.045% (w/w), about 0.046% (w/w), about 0.047% (w/w), about 0.048% (w/w), about 0.049% (w/w), about 0.05% (w/w), about 0.051% (w/w), about 0.052% (w/w), about 0.053% (w/w), about 0.054% (w/w), about 0.055% (w/w), about 0.056% (w/w), about 0.057% (w/w), about 0.058% (w/w), about 0.059% (w/w), about 0.06% (w/w), about 0.061% (w/w), about 0.062% (w/w), about 0.063% (w/w), about 0.064% (w/w), about 0.065% (w/w), about 0.066% (w/w), about 0.067% (w/w), about 0.068% (w/w), about 0.069% (w/w), about 0.07% (w/w), about 0.071% (w/w), about 0.072% (w/w), about 0.073% (w/w), about 0.074% (w/w), about 0.075% (w/w), about 0.076% (w/w), about 0.077% (w/w), about 0.078% (w/w), about 0.079% (w/w), about 0.08% (w/w), about 0.081% (w/w), about 0.082% (w/w), about 0.083% (w/w), about 0.084% (w/w), about 0.085% (w/w), about 0.086% (w/w), about 0.087% (w/w), about 0.088% (w/w), about 0.089% (w/w), about 0.09% (w/w), about 0.091% (w/w), about 0.092% (w/w), about 0.093% (w/w), about 0.094% (w/w), about 0.095% (w/w), about 0.096% (w/w), about 0.097% (w/w), about 0.098% (w/w), about 0.099% (w/w), about 0.1% (w/w), about 0.2% (w/w), about 0.3% (w/w), about 0.4% (w/w), about 0.5% (w/w), about 0.6% (w/w), about 0.7% (w/w), about 0.8% (w/w), about 0.9% (w/w), about 1.0% (w/w), about 1.1% (w/w), about 1.2% (w/w), about 1.3% (w/w), about 1.4% (w/w), about 1.5% (w/w), about 1.6% (w/w), about 1.7% (w/w), about 1.8% (w/w), about 1.9% (w/w), about 2.0% (w/w), about 2.1% (w/w), about 2.2% (w/w), about 2.3% (w/w), about 2.4% (w/w), about 2.5% (w/w), about 2.6% (w/w), about 2.7% (w/w), about 2.8% (w/w), about 2.9% (w/w), about 3.0% (w/w), about 3.1% (w/w), about 3.2% (w/w), about 3.3% (w/w), about 3.4% (w/w), about 3.5% (w/w), about 3.6% (w/w), about 3.7% (w/w), about 3.8% (w/w), about 3.9% (w/w), about 4.0% (w/w), about 4.1% (w/w), about 4.2% (w/w), about 4.3% (w/w), about 4.4% (w/w), about 4.5% (w/w), about 4.6% (w/w), about 4.7% (w/w), about 4.8% (w/w), about 4.9% (w/w), about 5.0% (w/w), about 5.1% (w/w), about 5.2% (w/w), about 5.3% (w/w), about 5.4% (w/w), about 5.5% (w/w), about 5.6% (w/w), about 5.7% (w/w), about 5.8% (w/w), about 5.9% (w/w), about 6.0% (w/w), about 6.5% (w/w), about 7.0% (w/w), about 7.5% (w/w), about 8.0% (w/w), about 8.5% (w/w), about 9.0% (w/w), about 9.5% (w/w), about 10.0% (w/w), about 10.5% (w/w), about 11.0% (w/w), about 11.5% (w/w), about 12.0% (w/w), about 12.5% (w/w), about 13.0% (w/w), about 13.5% (w/w), about 14.0% (w/w), about 14.5% (w/w), and about 15.0% (w/w). In various embodiments, surfactants include, but are not limited to the following: Polysorbate 80 (about 0.1 to about 8% (w/w)), Tyloxapol (about 0.01 to about 1.0% (w/w)), Polyoxyl 35 castor oil (about 0.1 to about 12% (w/w)), Nonoxynol-9 (about 0.01 to about 1.0% (w/w)), Polyoxyl 40 hydrogenated castor oil (about 0.1 to about 10% (w/w)), Polyoxyl 15 hydroxystearate (about 0.01 to about 1.5% (w/w)), Polysorbate 20 (about 0.1 to about 1% (w/w)), Octoxynol-40 (about 0.01 to about 1% (w/w)), Poloxamer 407 (about 0.1 to about 35% (w/w)), Poloxamer 188 (about 0.1 to about 35% (w/w)), Carbomer copolymer type A (about 0.001 to about 1% (w/w)), and Carbomer copolymer type B (about 0.001 to about 1% (w/w)).

Eye irritancy of surfactants decreases in the order of cationic (positively charged) surfactants, anionic surfactants (negatively charged), ampholytic (both positively and negatively charged) and nonionic surfactants (no formal charge). In some embodiments, nonionic surfactants can be used at higher concentrations without causing irritation. Additionally, nonionic surfactants can be utilized at any pH, including pHs that are close to physiological pH. Ionic surfactant properties vary with pH and are optimized in defined pH ranges. The choice of nonionic surfactants in this invention are based upon their ability to produce microemulsions that are optically clear (or nearly optically clear), spread easily over a hydrophobic surface, and improve (or not interfere with) lubricity. In certain embodiments, the surfactants are nonionic surfactants such as Polyoxyl 35 castor oil (NF) (Cremophor EL) (RN: 61791-12-6), Polyoxyl 40 hydrogenated castor oil (NF) (Cremophor RH) (RN: 61788-85-0), and Ethylene oxide/propylene oxide copolymer (Poloxamer 407) (RN: 977057-91-2). In an embodiment, a nearly optically clear microemulsion was prepared from lanolin solubilized in a plant oil (e.g., castor oil) in combination with a nonionic surfactant.

The lipids of the tear film include mostly neutral lipids (wax esters, cholesteryl esters, free cholesterol, and triacylglycerols), some polar lipid components (free fatty acids), and some amphiphilic phospholipids. In another embodiment, the present invention includes ophthalmic pharmaceutical compositions comprising one or more of the following plant oil components: castor oil, flaxseed oil, sesame seed oil, sea buckthorn seed oil, sea buckthorn pulp oil, perilla seed oil, chia seed oil, pecan nut oil, macadamia nut oil, and rosehip seed oil. In another embodiment, the present invention includes ophthalmic pharmaceutical compositions comprising a fish oil. In another embodiment, the present invention includes ophthalmic pharmaceutical compositions comprising a plant or fish oil (such as anchovy oil) with less than 1% Palmitic Acid and/or a fish oil (such as anchovy oil) component with a measured content of over 50% palmitoleic acid ethyl ester and less than 1% Palmitic Acid (such as the product Provinal®). In another embodiment, the present invention includes ophthalmic pharmaceutical compositions comprising one or more of the following lipids: lanolin, anhydrous lanolin, cetyl alcohol, lanolin alcohols, and glyceryl monostearate.

In some embodiments, the total amount of lipid(s) and/or oil(s) in the formulation will approach up to about 0.05% (w/w), or up to about 0.1% (w/w), or up to about 0.15% (w/w), or up to about 0.2% (w/w), or up to about 0.25% (w/w), or up to about 0.5% (w/w), or up to about 1% (w/w), or up to about 2% (w/w). In some embodiments, the ophthalmic pharmaceutical formulations may comprise about 0.0025% (w/w) to about 2% (w/w) lipid(s) and/or oil(s). In other embodiments, the ophthalmic pharmaceutical formulations may comprise about 0.01% (w/w) to about 0.5% (w/w) lipid(s) and/or oil(s). In still other embodiments, the ophthalmic pharmaceutical formulations may comprise a lipid(s) and/or oil(s) portion comprising one or more lipid(s) and/or oil(s) in an amount selected from the group consisting of about 0.01% (w/w), about 0.02% (w/w), about 0.03% (w/w), about 0.04% (w/w), about 0.05% (w/w), about 0.06% (w/w), about 0.07% (w/w), about 0.08% (w/w), about 0.09% (w/w), about 0.1% (w/w), about 0.11% (w/w), about 0.12% (w/w), about 0.13% (w/w), about 0.14% (w/w), about 0.15% (w/w), about 0.16% (w/w), about 0.17% (w/w), about 0.18%

(w/w), about 0.19% (w/w), about 0.2% (w/w), about 0.21% (w/w), about 0.22% (w/w), about 0.23% (w/w), about 0.24% (w/w), and about 0.25% (w/w). In various embodiments, specific lipid(s) and/or oil(s) component concentrations include, but are not limited to the following: Castor oil (about 0.001 to about 5.0% (w/w)), Flaxseed oil (about 0.001 to about 5.0% (w/w)), Sesame Seed oil (about 0.001 to about 5.0% (w/w)), Sea Buckthorn Seed oil (about 0.001 to about 5.0% (w/w)), Sea Buckthorn Pulp oil (about 0.001 to about 5.0% (w/w)), Perilla Seed oil (about 0.001 to about 5.0% (w/w)), Chia Seed oil (about 0.001 to about 5.0% (w/w)), Pecan Nut oil (about 0.001 to about 5.0% (w/w)), Macadamia Nut oil (about 0.001 to about 5.0% (w/w)), Rosehip Seed oil (about 0.001 to about 5.0% (w/w)), Anchovy oil (about 0.001 to about 5.0% (w/w)), Lanolin (about 0.001 to about 1.0% (w/w)), Anhydrous Lanolin (about 0.001 to about 1.0% (w/w)), Cetyl Alcohol (about 0.001 to about 1.0% (w/w)), Lanolin Alcohols (about 0.001 to about 1.0% (w/w)), and Glyceryl Monostearate (about 0.001 to about 1.0% (w/w)).

Mucoadhesive polymers have an attraction to the mucus layer covering the eye. This results in the polymers being retained in the eye for a long period of time. Hyaluronic acid (HA) is an endogenous water-soluble mucoadhesive polymer that produces viscous and elastic gels with lubricative properties at various locations in the body. HA is known to be mucoadhesive and shear-thinning and is comfortable when administered to the eye. In an alternative, HA may be present in a base form, as a hyaluronate, such as sodium hyaluronate. The synthesized mucoadhesive polyacrylic polymer Carbomer may also be included in the ophthalmic pharmaceutical formulations. The inclusion of water-soluble polymers often increase the viscosity of the dry eye product which in turn increases the product's retention time. Some polymers are attracted to the mucin coating the ocular surface, and this mucoadhesive property of the polymer will increase retention time. Hyaluronic acid and carbomer are mucoadhesive, increase viscosity, and effectively retain water. In an embodiment, the present invention includes ophthalmic pharmaceutical compositions comprising one or more of the following mucoadhesive polymers: sodium hyaluronate or hyaluronic acid (hyaluronan), hyaluronic acid derivatives, poly(acrylic acid), carbomer copolymer type A, carbomer copolymer type B, polyacrylic acid derivatives, polycarbophil, chitosan, chitosan derivatives, O-carboxymethyl chitosan, N-carboxymethyl chitosan, alginic acid, alginic acid derivatives, guar, guar derivatives, hydroxypropyl guar, hydroxypropyl guar derivatives, gellan gum, gellan gum derivatives, pectin, pectin derivatives, carrageenan, carrageenan derivatives, gelatin, poloxamer, xanthan, xanthan derivatives, xyloglucan, xyloglucan derivatives, poly (D,L lactide-coglycolide), tamarind gum polysaccharide, and arabinogalactan.

In some embodiments, the ophthalmic pharmaceutical formulations comprise mucoadhesive polymers in an amount up to about 2% (w/w), or up to about 3% (w/w), or up to about 4% (w/w). In some embodiments, the ophthalmic pharmaceutical formulations comprise mucoadhesive polymers in an amount ranging from about 0.001% (w/w) to about 2% (w/w), or from about 0.001% (w/w) to about 3% (w/w), or from about 0.001% (w/w) to about 4% (w/w). In still other embodiments, the ophthalmic pharmaceutical formulations may comprise one or more mucoadhesive polymers in a total amount selected from the group consisting of about 0.01% (w/w), about 0.02% (w/w), about 0.03% (w/w), about 0.04% (w/w), about 0.05% (w/w), about 0.06% (w/w), about 0.07% (w/w), about 0.08% (w/w), about 0.09% (w/w), about 0.1% (w/w), about 0.11% (w/w), about 0.12% (w/w), about 0.13% (w/w), about 0.14% (w/w), about 0.15% (w/w), about 0.16% (w/w), about 0.17% (w/w), about 0.18% (w/w), about 0.19% (w/w), about 0.2% (w/w), about 0.21% (w/w), about 0.22% (w/w), about 0.23% (w/w), about 0.24% (w/w), about 0.25% (w/w), about 0.26% (w/w), about 0.27% (w/w), about 0.28% (w/w), about 0.29% (w/w), about 0.3% (w/w), about 0.31% (w/w), about 0.32% (w/w), about 0.33% (w/w), about 0.34% (w/w), about 0.35% (w/w), about 0.36% (w/w), about 0.37% (w/w), about 0.38% (w/w), about 0.39% (w/w), about 0.4% (w/w), about 0.41% (w/w), about 0.42% (w/w), about 0.43% (w/w), about 0.44% (w/w), about 0.45% (w/w), about 0.46% (w/w), about 0.47% (w/w), about 0.48% (w/w), about 0.49% (w/w), about 0.5% (w/w), about 0.51% (w/w), about 0.52% (w/w), about 0.53% (w/w), about 0.54% (w/w), about 0.55% (w/w), about 0.56% (w/w), about 0.57% (w/w), about 0.58% (w/w), about 0.59% (w/w), about 0.6% (w/w), about 0.61% (w/w), about 0.62% (w/w), about 0.63% (w/w), about 0.64% (w/w), about 0.65% (w/w), about 0.66% (w/w), about 0.67% (w/w), about 0.68% (w/w), about 0.69% (w/w), about 0.7% (w/w), about 0.71% (w/w), about 0.72% (w/w), about 0.73% (w/w), about 0.74% (w/w), about 0.75% (w/w), about 0.76% (w/w), about 0.77% (w/w), about 0.78% (w/w), about 0.79% (w/w), about 0.8% (w/w), about 0.81% (w/w), about 0.82% (w/w), about 0.83% (w/w), about 0.84% (w/w), about 0.85% (w/w), about 0.86% (w/w), about 0.87% (w/w), about 0.88% (w/w), about 0.89% (w/w), about 0.9% (w/w), about 0.91% (w/w), about 0.92% (w/w), about 0.93% (w/w), about 0.94% (w/w), about 0.95% (w/w), about 0.96% (w/w), about 0.97% (w/w), about 0.98% (w/w), about 0.99% (w/w), about 1.0%, about 1.1% (w/w), about 1.2% (w/w), about 1.3% (w/w), about 1.4% (w/w), about 1.5% (w/w), about 1.6% (w/w), about 1.7% (w/w), about 1.8% (w/w), about 1.9% (w/w), about 2.0% (w/w), about 2.1% (w/w), about 2.2% (w/w), about 2.3% (w/w), about 2.4% (w/w), about 2.5% (w/w), about 2.6% (w/w), about 2.7% (w/w), about 2.8% (w/w), about 2.9% (w/w), and about 3.0% (w/w).

Mucoadhesive polymers (alone or in any combination) that lubricate mucous membrane surfaces and relieve dryness and irritation include: sodium hyaluronate or hyaluronic acid (hyaluronan) (about 0.001 to about 3% (w/w)), hyaluronic acid derivatives (about 0.001 to about 3% (w/w)), carbomer (about 0.001 to about 3% (w/w)), poly(acrylic acid) (about 0.001 to about 3% (w/w)), poly (acrylic acid) derivatives (about 0.001 to about 3% (w/w)), carbomer copolymer type A (about 0.001 to about 3% (w/w)), carbomer copolymer type B (about 0.001 to about 3% (w/w)), carbomer polyacrylic acid derivatives (about 0.001 to about 3% (w/w)), polycarbophil (about 0.01 to about 2% (w/w)), chitosan (about 0.001 to about 2% (w/w)), chitosan derivatives (about 0.001 to about 3% (w/w)), O-carboxymethyl chitosan (about 0.01 to about 3% (w/w)), N-carboxymethyl chitosan (about 0.01 to about 3% (w/w)), alginic acid (about 0.01 to about 3% (w/w)), alginic acid derivatives (about 0.01 to about 3% (w/w)), guar (about 0.01 to about 3% (w/w)), guar derivatives (about 0.001 to about 3% (w/w)), hydroxypropyl guar (about 0.01 to about 3% (w/w)), hydroxypropyl guar derivatives (about 0.01 to about 3% (w/w)), gellan gum (about 0.01 to about 3% (w/w)), gellan gum derivatives (about 0.001 to about 3% (w/w)), pectin (about 0.01 to about 3% (w/w)), pectin derivatives (about 0.01 to about 3% (w/w)), carrageenan (about 0.01 to about 3% (w/w)), carrageenan derivatives (about 0.01 to about 3% (w/w)), gelatin (about 0.01 to about 3% (w/w)), poloxamer (about 0.1 to about 35% (w/w)), xanthan (about 0.1 to about 3% (w/w)), xanthan derivatives (about 0.1 to about 3% (w/w)), xyloglucan (about 0.1 to about 3% (w/w)), xyloglucan derivatives (about 0.1 to about 3% (w/w)), Poly (D,L lactide-coglycolide) (about 0.1 to about 3% (w/w)), tamarind gum polysaccharide (about 0.1 to about 3% (w/w)), and arabinogalactan (about 0.1 to about 3% (w/w)).

Proper nutritional support is needed for healthy eyes, which includes the avascular cornea. Historically, meeting ocular nutritional needs was (and is) focused on oral administration of nutrients with adsorption from the gastrointestinal track into the blood stream. The nutrients are then transferred from the blood to the ocular glands responsible for producing tear fluid. However, the ophthalmic pharmaceutical formulations of the invention provide ingredients for nutritional supplementation directly to the cornea. In an embodiment, the ophthalmic pharmaceutical formulations of the invention contain energy sources such as dextrose or mannitol or sorbitol and fatty acids and/or triglycerides. Essential fatty acids are often selected since they cannot be synthesized in the body. Vitamins and amino acids may be included to facilitate general cell health. In certain embodiments the ophthalmic pharmaceutical formulations comprise ingredients for nutritional supplementation including saturated, monounsaturated, and polyunsaturated fatty acids, and triglycerides. Specific fatty acids may include (but are not limited to) ricinoleic acid, palmitoleic acid, linoleic acid, alpha-linolenic acid, linolenic acid, stearic acid, arachidic acid, heptadecanoic acid, oleic acid, stearidonic acid, eicosapentaenoic acid, and docosahexaenoic acid. In additional embodiments, the ophthalmic pharmaceutical formulations comprise ingredients for nutritional supplementation including vitamins such as (but not limited to) ascorbic acid (vitamin C) and derivatives thereof such as ascorbyl palmitate, vitamin E and derivatives thereof, and vitamin D and derivatives thereof. In other embodiments, the ingredients for nutritional supplementation includes 1) vitamin C and trisodium citrate, or 2) vitamin C and trisodium citrate and Ferulic acid, or 3) vitamin C and trisodium citrate and vitamin E, or 4) vitamin C and trisodium citrate and Vitamin E and Ferulic acid, or 5) ascorbyl palmitate and trisodium citrate or 6) ascorbyl palmitate and trisodium citrate and Ferulic acid or 7) ascorbyl palmitate and vitamin E and trisodium citrate or 8) ascorbyl palmitate and vitamin E and trisodium citrate and Ferulic acid. In further embodiments, the ophthalmic pharmaceutical formulations comprise ingredients for nutritional supplementation including amino acids such as (but not limited to) as Glutamic Acid, Serine, Phenylalanine, Aspartic Acid, Threonine, Leucine, Lysine, and Isoleucine.

In some embodiments, the ophthalmic pharmaceutical formulations comprise ingredients for nutritional supplementation in a total amount up to about 1% (w/w), or up to about 3% (w/w), or up to about 6% (w/w). In some embodiments, the ophthalmic pharmaceutical formulations comprise ingredients for nutritional supplementation in an amount ranging from about 0.001% (w/w) to about 2% (w/w), or from about 0.001% (w/w) to about 3% (w/w), or from about 0.001% (w/w) to about 4% (w/w). In still other embodiments, the ophthalmic pharmaceutical formulations may comprise one or more ingredients for nutritional supplementation in a total amount selected from the group consisting of about 0.01% (w/w), about 0.02% (w/w), about 0.03% (w/w), about 0.04% (w/w), about 0.05% (w/w), about 0.06% (w/w), about 0.07% (w/w), about 0.08% (w/w), about 0.09% (w/w), about 0.1% (w/w), about 0.11% (w/w), about 0.12% (w/w), about 0.13% (w/w), about 0.14% (w/w), about 0.15% (w/w), about 0.16% (w/w), about 0.17% (w/w), about 0.18% (w/w), about 0.19% (w/w), about 0.2% (w/w), about 0.21% (w/w), about 0.22% (w/w), about 0.23% (w/w), about 0.24% (w/w), about 0.25% (w/w), about 0.26% (w/w), about 0.27% (w/w), about 0.28% (w/w), about 0.29% (w/w), about 0.3% (w/w), about 0.31% (w/w), about 0.32% (w/w), about 0.33% (w/w), about 0.34% (w/w), about 0.35% (w/w), about 0.36% (w/w), about 0.37% (w/w), about 0.38% (w/w), about 0.39% (w/w), about 0.4% (w/w), about 0.41% (w/w), about 0.42% (w/w), about 0.43% (w/w), about 0.44% (w/w), about 0.45% (w/w), about 0.46% (w/w), about 0.47% (w/w), about 0.48% (w/w), about 0.49% (w/w), about 0.5% (w/w), about 0.51% (w/w), about 0.52% (w/w), about 0.53% (w/w), about 0.54% (w/w), about 0.55% (w/w), about 0.56% (w/w), about 0.57% (w/w), about 0.58% (w/w), about 0.59% (w/w), about 0.6% (w/w), about 0.61% (w/w), about 0.62% (w/w), about 0.63% (w/w), about 0.64% (w/w), about 0.65% (w/w), about 0.66% (w/w), about 0.67% (w/w), about 0.68% (w/w), about 0.69% (w/w), about 0.7% (w/w), about 0.71% (w/w), about 0.72% (w/w), about 0.73% (w/w), about 0.74% (w/w), about 0.75% (w/w), about 0.76% (w/w), about 0.77% (w/w), about 0.78% (w/w), about 0.79% (w/w), and about 0.8% (w/w).

In some embodiments, the ingredients for nutritional supplementation include, but are not limited to: Dextrose or Mannitol or Sorbitol (about 1 to about 6% (w/w)), Ascorbic Acid (about 0.0001 to about 0.4% (w/w)), Ascorbyl Palmitate (about 0.0005 to about 0.8% (w/w)), Vitamin D (about 0.0001 to about 0.3% (w/w)), Vitamin E (about 0.0001 to about 0.3% (w/w)), Glutamic Acid (about 0.0005 to about 0.8% (w/w)), Serine (about 0.0005 to about 0.5% (w/w)), Phenylalanine (about 0.0005 to about 0.8% (w/w)), Aspartic Acid (about 0.0005 to about 0.7% (w/w)), Threonine (about 0.0005 to about 0.6% (w/w)), Leucine (about 0.0001 to about 0.5% (w/w)), Lysine (about 0.0001 to about 0.4% (w/w)), and Isoleucine (about 0.0001 to about 0.2% (w/w)).

A comprehensive nutritional approach of including Ascorbic Acid (vitamin C) or salts or esters thereof (such as Ascorbyl Palmitate), vitamin D or salts or esters thereof, metabolically important tear fluid amino acids, and the energy source(s) of sugars such as dextrose or mannitol or sorbitol and/or fatty acids and/or triglycerides to promote corneal health is helpful for the DED patient. The combination of immediate symptom relief with long term corneal health results in products that patients are more likely to use and demonstrate long term improvements in corneal health. In an embodiment, formulations containing either ascorbic acid or Ascorbyl Palmitate also include trisodium citrate and/or ferulic acid to improve clarity and limit color change.

Tonicity and/or osmoprotectant agents may be added to the ophthalmic pharmaceutical formulations of the invention to ensure that the total osmolarity of the product is at the target value. In an embodiment, the target value is near 300 mOsm to match normal tear fluid osmolarity. The osmolality of tear fluid of dry eye patients is often higher than that seen in normal tear fluid. Therefore, the target value of dry eye products may be lower than 300 mOsm in order to counteract high tear osmolarity.

Tonicity and/or osmoprotectant agents that may be used in the ophthalmic pharmaceutical formulations include mannitol, inositol, sorbitol, polyethylene glycol (PEG), glucose, glycerin, glutamic acid, proline, betaine (which may also be known as trimethylglycine or glycine betaine), taurine, L-carnitine, trehalose, gamma-aminobutyric acid (GABA), alanine, arginine, glycine, glutamine, asparagine, ornithine, isoleucine, leucine, valine, putrescine, spermidine, spermine, homospermine, cadaverine, urea, and glycerophosphocholine. In some embodiments, the ophthalmic pharmaceutical formulations comprise one or more tonicity and/or osmoprotectant agents in a total amount up to about 5%

(w/w), or up to about 7% (w/w), or up to about 10% (w/w). In some embodiments, the ophthalmic pharmaceutical formulations comprise one or more tonicity and/or osmoprotectant agents in an amount ranging from about 0.5% (w/w) to about 5% (w/w), or from about 0.5% (w/w) to about 7% (w/w), or from about 0.5% (w/w) to about 10% (w/w).

In some embodiments, the ingredients used as tonicity and/or osmoprotectant agents for adjusting product osmolarity and/or offering protection from hyperosmotic conditions include, but are not limited to: mannitol (about 0.05 to about 6% (w/w)), inositol (about 0.05 to about 6% (w/w)), sorbitol (about 0.05 to about 6% (w/w)), polyethylene glycol (PEG) (about 0.5 to about 3% (w/w)), dextrose (about 0.5 to about 6% (w/w)), glycerin (about 0.05 to about 7% (w/w)), glutamic acid (about 0.0005 to about 0.8% (w/w)), proline (about 0.0005 to about 0.8% (w/w)), betaine (about 0.0005 to about 0.8% (w/w)), Taurine (about 0.0005 to about 0.8% (w/w)), L-carnitine (about 0.0005 to about 0.8% (w/w)), Gamma-aminobutyric acid (GABA) (about 0.0005 to about 0.8% (w/w)), Trehalose (about 0.1 to about 5% (w/w)), Alanine (about 0.5 to about 3% (w/w)), Arginine (about 0.5 to about 3% (w/w)), Glycine (about 0.5 to about 3% (w/w)), Glutamine (about 0.5 to about 3% (w/w)), Asparagine (about 0.5 to about 3% (w/w)), Ornithine (about 0.5 to about 3% (w/w)), Isoleucine (about 0.5 to about 3% (w/w)), Leucine (about 0.5 to about 3% (w/w)), Valine (about 0.5 to about 3% (w/w)), putrescine (about 0.5 to about 3% (w/w)), spermidine (about 0.5 to about 3% (w/w)), spermine (about 0.5 to about 3% (w/w)), homospermine (about 0.5 to about 3% (w/w)), cadaverine (about 0.5 to about 3% (w/w)), urea (about 0.5 to about 3% (w/w), and glycerophosphocholine (about 0.5 to about 3% (w/w)).

In still other embodiments, the ophthalmic pharmaceutical formulations may comprise one or more tonicity and/or osmoprotectant agents in a total amount selected from the group consisting of about 0.01% (w/w), about 0.02% (w/w), about 0.03% (w/w), about 0.04% (w/w), about 0.05% (w/w), about 0.06% (w/w), about 0.07% (w/w), about 0.08% (w/w), about 0.09% (w/w), about 0.1% (w/w), about 0.11% (w/w), about 0.12% (w/w), about 0.13% (w/w), about 0.14% (w/w), about 0.15% (w/w), about 0.16% (w/w), about 0.17% (w/w), about 0.18% (w/w), about 0.19% (w/w), about 0.2% (w/w), about 0.21% (w/w), about 0.22% (w/w), about 0.23% (w/w), about 0.24% (w/w), about 0.25% (w/w), about 0.26% (w/w), about 0.27% (w/w), about 0.28% (w/w), about 0.29% (w/w), about 0.3% (w/w), about 0.31% (w/w), about 0.32% (w/w), about 0.33% (w/w), about 0.34% (w/w), about 0.35% (w/w), about 0.36% (w/w), about 0.37% (w/w), about 0.38% (w/w), about 0.39% (w/w), about 0.4% (w/w), about 0.41% (w/w), about 0.42% (w/w), about 0.43% (w/w), about 0.44% (w/w), about 0.45% (w/w), about 0.46% (w/w), about 0.47% (w/w), about 0.48% (w/w), about 0.49% (w/w), about 0.5% (w/w), about 0.51% (w/w), about 0.52% (w/w), about 0.53% (w/w), about 0.54% (w/w), about 0.55% (w/w), about 0.56% (w/w), about 0.57% (w/w), about 0.58% (w/w), about 0.59% (w/w), about 0.6% (w/w), about 0.61% (w/w), about 0.62% (w/w), about 0.63% (w/w), about 0.64% (w/w), about 0.65% (w/w), about 0.66% (w/w), about 0.67% (w/w), about 0.68% (w/w), about 0.69% (w/w), about 0.7% (w/w), about 0.71% (w/w), about 0.72% (w/w), about 0.73% (w/w), about 0.74% (w/w), about 0.75% (w/w), about 0.76% (w/w), about 0.77% (w/w), about 0.78% (w/w), about 0.79% (w/w), about 0.8% (w/w), about 0.81% (w/w), about 0.82% (w/w), about 0.83% (w/w), about 0.84% (w/w), about 0.85% (w/w), about 0.86% (w/w), about 0.87% (w/w), about 0.88% (w/w), about 0.89% (w/w), about 0.9% (w/w), about 0.91% (w/w), about 0.92% (w/w), about 0.93% (w/w), about 0.94% (w/w), about 0.95% (w/w), about 0.96% (w/w), about 0.97% (w/w), about 0.98% (w/w), about 0.99% (w/w), about 1.0%, about 1.1% (w/w), about 1.2% (w/w), about 1.3% (w/w), about 1.4% (w/w), about 1.5% (w/w), about 1.6% (w/w), about 1.7% (w/w), about 1.8% (w/w), about 1.9% (w/w), about 2.0% (w/w), about 2.1% (w/w), about 2.2% (w/w), about 2.3% (w/w), about 2.4% (w/w), about 2.5% (w/w), about 2.6% (w/w), about 2.7% (w/w), about 2.8% (w/w), about 2.9% (w/w), about 3.0% (w/w), about 3.1% (w/w), about 3.2% (w/w), about 3.3% (w/w), about 3.4% (w/w), about 3.5% (w/w), about 3.6% (w/w), about 3.7% (w/w), about 3.8% (w/w), about 3.9% (w/w), about 4.0%, about 4.1% (w/w), about 4.2% (w/w), about 4.3% (w/w), about 4.4% (w/w), about 4.5% (w/w), about 4.6% (w/w), about 4.7% (w/w), about 4.8% (w/w), about 4.9% (w/w), and about 5.0% (w/w).

Dry eye patients have many symptoms, but the relief of dryness is a primary concern. Hence, the pharmaceutical ophthalmic formulations of the present invention include water to hydrate the cells of the eye. The water used in the examples is distilled water and prevents the introduction of ionic species into the example products. Purified water (or water for injection) may be used in a manufacturing environment with the final product meeting specified sterility requirements.

The pharmaceutical ophthalmic formulations of the present invention are administered directly to the eye and give immediate hydration. Patients with chronic dry eye may administer several drops a day. In an embodiment, the pharmaceutical ophthalmic formulations of the present invention are preservative free.

The tear film of the eye is normally maintained at a pH of about 7.4. In an embodiment, the pH of the pharmaceutical ophthalmic formulations of the present invention is adjusted to a comfortable level, such as about 7.4, or such as about 6.8 to about 7.8, with a pH adjusting agent. The pH of the tear may increase with time to higher and uncomfortable pH levels. High uncomfortable pH levels are often seen in patients suffering from DED. Conversely, the administration of strongly buffered products with a pH of 5 or lower causes pain and possible damage when administered to the eye. In certain embodiments, the pH adjusting agent is tromethamine. In other embodiments, the pH adjusting agent is a base, such as sodium hydroxide, or an acid, such as hydrochloric acid or ascorbic acid. In additional embodiments, the pH adjusting agent includes a buffer, such as a phosphate buffer or disodium phosphate. Tromethamine acts as a weak buffer system, along with charged polymers (hyaluronic acid, carbomer, polyvinyl pyrrolidone) and amino acids.

The pharmaceutical ophthalmic formulations of the present invention are manufactured by conventional techniques. The general manufacturing procedure is dictated by whether the formulation contains a surfactant, a mucoadhesive polymer and/or an oil(s). More detail is provided for certain types of formulations of the invention in the following paragraphs and in the examples.

For formulations that contain a demulcent and surfactant(s), a measured amount of demulcent is added to the mixing vessel. A measured amount of surfactant(s) is then added with agitation to the mixing vessel. Alternatively, the demulcent can be added after the surfactant(s) is incorporated into the batch. Agitation is applied until a clear solution is obtained. A tonicity and/or osmoprotectant agent (e.g., mannitol) is added and a possible buffer agent (such as disodium phosphate) is added with agitation. Agitation is applied until a clear solution is obtained. Purified water (or water for injection) is added to reach about 80% of target weight and mixed to achieve batch uniformity. If needed, tromethamine solution and/or hydrochloric acid is used to adjust the pH to a target pH of 7.4, but within the pH range of 6.8 to 7.8. Sufficient purified water (or water for injection) is added to bring the batch weight to the target weight value.

For formulations that contain a demulcent, surfactant(s), and a mucoadhesive polymer(s), a measured amount of mucoadhesive polymer (e.g., sodium hyaluronate) is added to the mixing vessel. Measured amounts of surfactant(s) is then added with agitation to the mixing vessel. A measured amount of demulcent is added to the mixing vessel with agitation. Alternatively, the mucoadhesive polymer(s) and/or the demulcent can be added after surfactant(s) is incorporated into the batch. Agitation is applied until a clear solution is obtained. A tonicity and/or osmoprotectant agent (e.g., mannitol) is added with agitation. Purified water (or water for injection) is added to reach about 80% of target weight and mixed to achieve batch uniformity. If needed, tromethamine solution and/or hydrochloric acid is used to adjust the pH to a target pH of 7.4, but within the pH range of 6.8 to 7.8. Sufficient purified water (or water for injection) is added to bring the batch weight to the target weight value.

For formulations that contain a demulcent, surfactants, an oil(s), and optionally a mucoadhesive polymer, a measured amount of oil(s) is added to the mixing vessel. Measured amounts of surfactant(s) are then added with agitation to the mixing vessel. The critical manufacturing step of mixing until a clear solution is obtained is then performed. Measured amount of demulcent is added to the mixing vessel with agitation. If included in the formulation a measured amount of mucoadhesive polymer (e.g., sodium hyaluronate) is added to the mixing vessel. Alternatively, the mucoadhesive polymer(s) can be added before the demulcent is incorporated into the batch. Agitation is applied until a clear solution is obtained. If included in the formulation a measured amount of buffer (e.g., disodium phosphate) is added to the mixing vessel. A tonicity and/or osmoprotectant agent (e.g., mannitol) is added with agitation. Purified water (or water for injection) is added to reach about 80% of target weight and mixed to achieve batch uniformity. If needed, tromethamine solution and/or hydrochloric acid is used to adjust the pH to a target pH of 7.4, but within the pH range of 6.8 to 7.8. Sufficient purified water (or water for injection) is added to bring the batch weight to the target weight value.

If the formulation includes lanolin, then an additional manufacturing step is included in which lanolin is added to an oil(s) to make a clear lanolin in oil solution. The lanolin oil(s) solution is then treated as an oil in regard to manufacturing the product.

If the formulation includes ascorbic acid, then the ascorbic acid can be added before or after surfactant(s) is present If the formulation includes Ascorbyl palmitate, then an additional manufacturing step is included. A clear stock solution containing sufficient surfactant(s) to solubilize Ascorbyl palmitate is manufactured. Alternatively, the addition of Ascorbyl palmitate may take place after the surfactant(s) is added.

If the formulation includes Amino Acids, then an additional manufacturing step is included. A clear stock solution of the amino acids is manufactured at concentrations facilitating reasonable manufacture. Preferably the addition of the stock solution takes place after surfactant(s) addition for those formulations containing surfactant(s).

The formulations of the present invention may be used as a platform to which additional pharmaceutically active agents may be added for administration to the eye of a patient to treat an ocular condition.

The formulations of the present invention are administered to the eye of a patient in need of treatment, such as a person suffering from DED, in an amount effective to treat or ameliorate symptoms of DED or provide relief or amelioration of discomfort.

EXAMPLES

Example 1

| Formulation SH-7 | |
|---|---|
| Ingredient | Percent (w/w) |
| Povidone K-90 | 1.5% |
| Poloxamer 407 | 2% |
| Sodium Hyaluronate | 0.1% |
| Carbomer Copolymer Type B | 0.005% |
| Mannitol | 4% |
| Tromethamine | Sufficient quantity to adjust product pH from 6.8 to 7.8 |
| Hydrochloric Acid | Sufficient quantity to adjust product pH from 6.8 to 7.8 |
| Distilled Water | Sufficient quantity to adjust batch weight to 100% of target |

Weighed amounts of 1% (w/w) Sodium Hyaluronate solution (pH adjusted to 6.8-7.8), 10% (w/w) Poloxamer 407 solution, 5% (w/w) povidone K-90 solution (pH adjusted to 6.8-7.8), and mannitol were added in order and with agitation to a beaker containing a stir bar. The pH of the stock solutions was preadjusted so that the final product pH ranges from 6.8 to 7.8. A sufficient amount of distilled water was added to reach about 80% of the target weight and the ingredients were stirred until it appeared that the product was in solution. Distilled water was added to bring the final batch weight to target weight.

Example 2

| Test Formulation FT-1 | |
|---|---|
| Ingredient | Percent (w/w) |
| Povidone K-90 | 2% |
| Cremophor EL | 5% |
| Poloxamer 407 | 2% |
| Carbomer Copolymer Type B | 0.005% |
| Disodium Phosphate | 0.3% |
| Mannitol | 3% |
| Tromethamine | Sufficient quantity to adjust product pH from 6.8 to 7.8 |
| Hydrochloric Acid | Sufficient quantity to adjust product pH from 6.8 to 7.8 |
| Distilled Water | Sufficient quantity to adjust batch weight to 100% of target |

Weighed amounts of Cremophor EL, Poloxamer 407, 0.5% (w/w) Carbomer Copolymer Type B solution (pH adjusted to 6.8-7.8), 5% (w/w) Povidone K-90 solution (pH adjusted to 6.8-7.8), 0.75% (w/w) disodium phosphate solution (pH adjusted to 6.8-7.8), and 7.5% (w/w) mannitol solution were added in order and with agitation to a beaker containing a stir bar. The pH of the stock solutions was preadjusted so that the final product pH ranged from 6.8 to 7.8. The ingredients were stirred until it appeared that the product was in solution. Distilled water was added to bring the final batch weight to target weight.

Example 3

| Test Formulation FT-4 | |
|---|---|
| Ingredient | Percent (w/w) |
| Povidone K-90 | 2% |
| Cremophor RH | 1% |
| Poloxamer 407 | 2% |
| Carbomer Copolymer Type B | 0.005% |
| Disodium Phosphate | 0.3% |
| Mannitol | 3% |
| Tromethamine | Sufficient quantity to adjust product pH from 6.8 to 7.8 |
| Hydrochloric Acid | Sufficient quantity to adjust product pH from 6.8 to 7.8 |
| Distilled Water | Sufficient quantity to adjust batch weight to 100% of target |

Weighed amounts of Cremophor RH, Poloxamer 407, 0.5% (w/w) Carbomer Copolymer Type B solution (pH adjusted to 6.8-7.8), 5% (w/w) Povidone K-90 solution (pH adjusted to 6.8-7.8), 0.75% (w/w) disodium phosphate solution (pH adjusted to 6.8-7.8), and 7.5% (w/w) mannitol solution were added in order and with agitation to a beaker containing a stir bar. The pH of the stock solutions was preadjusted so that the final product pH ranges from 6.8 to 7.8. The ingredients were stirred until it appeared that the product was in solution. Distilled water was added to bring the final batch weight to target weight.

Example 4

| Test Formulation FTCO-1 | |
|---|---|
| Ingredient | Percent (w/w) |
| Povidone K-90 | 2% |
| Cremophor EL | 5% |
| Cremophor RH | 1% |
| Castor Oil | 0.15% |
| Carbomer Copolymer Type B | 0.005% |
| Disodium Phosphate | 0.3% |
| Mannitol | 3% |
| Tromethamine | Sufficient quantity to adjust product pH from 6.8 to 7.8 |
| Hydrochloric Acid | Sufficient quantity to adjust product pH from 6.8 to 7.8 |
| Distilled Water | Sufficient quantity to adjust batch weight to 100% of target |

A weighed amount of Castor Oil was added to weighed amounts of Cremophor EL and Cremophor RH in a beaker containing a stir bar and the ingredients were mixed until clear. Weighed amounts of 0.5% (w/w) Carbomer Copolymer Type B solution (pH adjusted to 6.8-7.8), 5% (w/w) Povidone K-90 solution (pH adjusted to 6.8-7.8), 0.75% (w/w) disodium phosphate (pH adjusted to 6.8-7.8), and 7.5% (w/w) mannitol solution were added. The pH of the stock solutions was preadjusted so that the final product pH ranged from 6.8 to 7.8. The ingredients were stirred until it appeared that the product was in solution. Distilled water was added to bring the final batch weight to target weight.

Example 5

| Test Formulation FTCOL-1 | |
|---|---|
| Ingredient | Percent (w/w) |
| Povidone K-90 | 2% |
| Cremophor EL | 5% |
| Cremophor RH | 1% |
| Castor Oil | 0.15% |
| Lanolin | 0.04% |
| Carbomer Copolymer Type B | 0.005% |
| Disodium Phosphate | 0.3% |
| Mannitol | 3% |
| Tromethamine | Sufficient quantity to adjust product pH from 6.8 to 7.8 |
| Hydrochloric Acid | Sufficient quantity to adjust product pH from 6.8 to 7.8 |
| Distilled Water | Sufficient quantity to adjust batch weight to 100% of target |

A weighed amount of lanolin was combined with a weighed amount of castor oil in a beaker complete with a stir bar and the mixture was placed in a 50° C. water bath until the lanolin was observed to melt. The mixture was transferred to a hot plate/magnetic stirrer (hot to touch) and mixed until the lanolin was "dissolved" in the Castor Oil and made a clear slightly yellow solution. Weighed amounts of the Lanolin in Castor Oil solution was added to weighed amounts of Cremophor EL and Cremophor RH and the ingredients were mixed until clear. Weighed amounts of 0.5% (w/w) Carbomer Copolymer Type B solution (pH adjusted to 6.8-7.8), 5% (w/w) Povidone K-90 solution (pH adjusted to 6.8-7.8), 0.75% (w/w) disodium phosphate solution (pH adjusted to 6.8-7.8), and 7.5% (w/w) mannitol solution were added in order and with agitation. The pH of the stock solutions was preadjusted so that the final product pH ranged from 6.8 to 7.8. The ingredients were stirred until it appeared that the product was in solution. Distilled water was added to bring the final batch weight to target weight.

Example 6

| Test Formulation ASC-1 | |
|---|---|
| Ingredient | Percent (w/w) |
| Sodium Hyaluronate | 0.1% |
| Poloxamer 407 | 2% |
| Povidone-K90 | 1.5% |
| Cremophor RH | 1% |
| Ascorbic Acid | 0.03% |
| Glutamic Acid | 0.084% |
| Serine | 0.061% |
| Phenylalanine | 0.037% |
| Aspartic Acid | 0.03% |
| Threonine | 0.028% |
| Leucine | 0.022% |
| Lysine | 0.014% |
| Dextrose | 4.63% |
| Tromethamine | Sufficient quantity to adjust product pH from 6.8 to 7.8 |
| Hydrochloric Acid | Sufficient quantity to adjust product pH from 6.8 to 7.8 |
| Distilled Water | Sufficient quantity to adjust batch weight to 100% of target |

A weighed amount of an appropriate concentration adjusted stock solution (pH adjusted to 6.8-7.8) that contained Cremophor RH, Ascorbic Acid, Glutamic Acid, Serine, Phenylalanine, Aspartic Acid, Threonine, Leucine, and Lysine was added to a beaker containing a stir bar. Weighed amounts of 1% (w/w) Sodium Hyaluronate solution, 10% (w/w) Poloxamer 407 solution, 5% (w/w) Povidone K-90 solution, and 5 g of dextrose were added in order and with agitation into a beaker. The pH of the stock solutions was preadjusted so that the final product pH ranged from 6.8 to 7.8. The ingredients were stirred until it appeared that the product was in solution. Distilled water was added to bring the final batch weight to target weight.

Example 7

| Test Formulation ASC-2 | |
|---|---|
| Ingredient | Percent (w/w) |
| Sodium Hyaluronate | 0.1% |
| Poloxamer 407 | 2% |
| Povidone-K90 | 1.5% |
| Cremophor RH | 1% |
| Ascorbic Acid | 0.03% |
| Trisodium Citrate | 0.55% |
| Glutamic Acid | 0.084% |
| Serine | 0.061% |
| Phenylalanine | 0.037% |
| Aspartic Acid | 0.03% |
| Threonine | 0.028% |
| Leucine | 0.022% |
| Lysine | 0.014% |
| Dextrose | 3.3% |
| Tromethamine | Sufficient quantity to adjust product pH from 6.8 to 7.8 |
| Hydrochloric Acid | Sufficient quantity to adjust product pH from 6.8 to 7.8 |
| Distilled Water | Sufficient quantity to adjust batch weight to 100% of target |

A weighed amount of an appropriate concentration adjusted (pH adjusted to 6.8-7.8) stock solution that contained Cremophor RH, Ascorbic Acid, Glutamic Acid, Serine, Phenylalanine, Aspartic Acid, Threonine, Leucine, and Lysine was added to a beaker containing a stir bar. Weighed amounts of 1% (w/w) Sodium Hyaluronate, 10% (w/w) Poloxamer 407 solution, 5% (w/w) Povidone K-90 solution, a weighed amount of Trisodium Citrate, and a weighed amount of dextrose were added in order and with agitation. The pH of the stock solutions was preadjusted so that the final product pH ranges from 6.8 to 7.8. The ingredients were stirred until it appeared that the product was in solution. Distilled water was added to bring the final batch weight to target weight.

Example 8

| Test Formulation ASC-3 | |
|---|---|
| Ingredient | Percent (w/w) |
| Sodium Hyaluronate | 0.1% |
| Poloxamer 407 | 2% |
| Povidone-K90 | 1.5% |
| Cremophor RH | 1% |
| Ascorbyl Palmitate | 0.075% |
| Glutamic Acid | 0.084% |
| Serine | 0.061% |
| Phenylalanine | 0.037% |
| Aspartic Acid | 0.03% |
| Threonine | 0.028% |
| Leucine | 0.022% |
| Lysine | 0.014% |
| Dextrose | 3.3% |
| Tromethamine | Sufficient quantity to adjust product pH from 6.8 to 7.8 |
| Hydrochloric Acid | Sufficient quantity to adjust product pH from 6.8 to 7.8 |
| Distilled Water | Sufficient quantity to adjust batch weight to 100% of target |

A weighed amount of an appropriate concentration adjusted stock solution (pH adjusted to 6.8-7.8) that contained Cremophor RH, Ascorbyl Palmitate, Glutamic Acid, Serine, Phenylalanine, Aspartic Acid, Threonine, Leucine, and Lysine was added to a beaker containing a stir bar. Weighed amounts of 1% (w/w) Sodium Hyaluronate solution, 10% (w/w) Poloxamer 407 solution, 5% (w/w) Povidone K-90 solution, and dextrose were added in order and with agitation. The pH of the stock solutions was preadjusted so that the final product pH ranged from 6.8 to 7.8. The ingredients were stirred until it appeared that the product was in solution. Distilled water was added to bring the final batch weight to target weight.

Example 9

| Test Formulation ASC-4 | |
|---|---|
| Ingredient | Percent |
| Sodium Hyaluronate | 0.1% |
| Poloxamer 407 | 2% |
| Povidone K90 | 1.5% |
| Cremophor RH | 1% |
| Ascorbyl Palmitate | 0.075% |
| Trisodium Citrate | 0.55% |
| Glutamic Acid | 0.084% |
| Serine | 0.061% |
| Phenylalanine | 0.037% |
| Aspartic Acid | 0.03% |
| Threonine | 0.028% |
| Leucine | 0.022% |
| Lysine | 0.014% |
| Dextrose | 3.3% |
| Tromethamine | Sufficient quantity to adjust product pH from 6.8 to 7.8 |
| Hydrochloric Acid | Sufficient quantity to adjust product pH from 6.8 to 7.8 |
| Distilled Water | Sufficient quantity to adjust batch weight to 100% of target |

A weighed amount of an appropriate concentration adjusted stock solution (pH adjusted to 6.8-7.8) that contained Cremophor RH, Ascorbyl Palmitate, Glutamic Acid, Serine, Phenylalanine, Aspartic Acid, Threonine, Leucine, and Lysine was added to a beaker containing a stir bar. Weighed amounts of 1% (w/w) Sodium Hyaluronate, 10% (w/w) Poloxamer 407 solution, 5% (w/w) Povidone K-90 solution, Trisodium Citrate, and dextrose were added in order and with agitation. The pH of the stock solutions was preadjusted so that the final product pH ranges from 6.8 to 7.8. The ingredients were stirred until it appeared that the product was in solution. Distilled water was added to bring the final batch weight to target weight.

Example 10

| Test Formulation ASC-5 | |
|---|---|
| Ingredient | Percent (w/w) |
| Sodium Hyaluronate | 0.1% |
| Poloxamer 407 | 2% |
| Povidone-K90 | 1.5% |
| Cremophor RH | 1% |
| Ascorbic Acid | 0.03% |
| Glutamic Acid | 0.084% |
| Serine | 0.061% |
| Phenylalanine | 0.037% |
| Aspartic Acid | 0.03% |
| Threonine | 0.028% |
| Leucine | 0.022% |
| Lysine | 0.014% |
| Isoleucine | 0.003% |
| Dextrose | 4.63% |
| Tromethamine | Sufficient quantity to adjust product pH from 6.8 to 7.8 |
| Hydrochloric Acid | Sufficient quantity to adjust product pH from 6.8 to 7.8 |
| Distilled Water | Sufficient quantity to adjust batch weight to 100% of target |

A weighed amount of an appropriate concentration adjusted stock solution (pH adjusted to 6.8-7.8) that contained Cremophor RH, Ascorbic Acid, Glutamic Acid, Serine, Phenylalanine, Aspartic Acid, Threonine, Leucine, Lysine, and Isoleucine was added to a beaker containing a stir bar. Weighed amounts of 1% (w/w) Sodium Hyaluronate solution, 10% (w/w) Poloxamer 407 solution, 5% (w/w) Povidone K-90 solution (pH adjusted to 6.8-7.8), and dextrose were added in order and with agitation. The pH of the stock solutions was preadjusted so that the final product pH ranged from 6.8 to 7.8. The ingredients were stirred until it appeared that the product was in solution. Distilled water was added to bring the final batch weight to target weight.

Example 11

| Test Formulation ASC-6 | |
|---|---|
| Ingredient | Percent (w/w) |
| Sodium Hyaluronate | 0.1% |
| Poloxamer 407 | 2% |
| Povidone-K90 | 1.5% |
| Cremophor RH | 1% |
| Ascorbic Acid | 0.03% |
| Trisodium Citrate | 0.55% |
| Glutamic Acid | 0.084% |
| Serine | 0.061% |
| Phenylalanine | 0.037% |
| Aspartic Acid | 0.03% |
| Threonine | 0.028% |
| Leucine | 0.022% |
| Lysine | 0.014% |
| Isoleucine | 0.003% |
| Dextrose | 3.3% |
| Tromethamine | Sufficient quantity to adjust product pH from 6.8 to 7.8 |
| Hydrochloric Acid | Sufficient quantity to adjust product pH from 6.8 to 7.8 |
| Distilled Water | Sufficient quantity to adjust batch weight to 100% of target |

A weighed amount of an appropriate concentration adjusted stock solution (pH adjusted to 6.8-7.8) that contained Cremophor RH, Ascorbic Acid, Glutamic Acid, Serine, Phenylalanine, Aspartic Acid, Threonine, Leucine, Lysine, and Isoleucine was added to a beaker containing a stir bar. Weighed amounts of 1% (w/w) Sodium Hyaluronate solution (pH adjusted to 6.8-7.8), 10% (w/w) Poloxamer 407 solution, 5% (w/w) Povidone K-90 solution (pH adjusted to 6.8-7.8), Trisodium Citrate, and dextrose were added in order and with agitation. The pH of the stock solutions was preadjusted so that the final product pH ranged from 6.8 to 7.8. The ingredients were stirred until it appeared that the product was in solution. Distilled water was added to bring the final batch weight to target weight.

Example 12

| Test Formulation ASC-7 | |
|---|---|
| Ingredient | Percent (w/w) |
| Sodium Hyaluronate | 0.1% |
| Poloxamer 407 | 2% |
| Povidone-K90 | 1.5% |
| Cremophor RH | 1% |
| Ascorbyl Palmitate | 0.075% |
| Glutamic Acid | 0.084% |
| Serine | 0.061% |
| Phenylalanine | 0.037% |
| Aspartic Acid | 0.03% |
| Threonine | 0.028% |
| Leucine | 0.022% |
| Lysine | 0.014% |
| Isoleucine | 0.003% |
| Dextrose | 3.3% |
| Tromethamine | Sufficient quantity to adjust product pH from 6.8 to 7.8 |
| Hydrochloric Acid | Sufficient quantity to adjust product pH from 6.8 to 7.8 |
| Distilled Water | Sufficient quantity to adjust batch weight to 100% of target |

A weighed amount of an appropriate concentration adjusted stock solution (pH adjusted to 6.8-7.8) that contained Cremophor RH, Ascorbyl Palmitate, Glutamic Acid, Serine, Phenylalanine, Aspartic Acid, Threonine, Leucine, Lysine, and Isoleucine was added to a beaker containing a stir bar. Weighed amounts of 1% (w/w) Sodium Hyaluronate (pH adjusted to 6.8-7.8), 10% (w/w) Poloxamer 407 solution, 5% (w/w) Povidone K-90 solution (pH adjusted to 6.8-7.8), and dextrose were added in order and with agitation. The pH of the stock solutions was preadjusted so that the final product pH ranged from 6.8 to 7.8. The ingredients were stirred until it appeared that the product was in solution. Distilled water was added to bring the final batch weight to target weight.

Example 13

| Test Formulation ASC-8 | |
|---|---|
| Ingredient | Percent |
| Sodium Hyaluronate | 0.1% |
| Poloxamer 407 | 2% |
| Povidone K90 | 1.5% |
| Cremophor RH | 1% |
| Ascorbyl Palmitate | 0.075% |
| Trisodium Citrate | 0.55% |
| Glutamic Acid | 0.084% |
| Serine | 0.061% |
| Phenylalanine | 0.037% |

-continued

Test Formulation ASC-8

| Ingredient | Percent |
| --- | --- |
| Aspartic Acid | 0.03% |
| Threonine | 0.028% |
| Leucine | 0.022% |
| Lysine | 0.014% |
| Isoleucine | 0.003% |
| Dextrose | 3.3% |
| Tromethamine | Sufficient quantity to adjust product pH from 6.8 to 7.8 |
| Hydrochloric Acid | Sufficient quantity to adjust product pH from 6.8 to 7.8 |
| Distilled Water | Sufficient quantity to adjust batch weight to 100% of target |

A weighed amount of an appropriate concentration stock solution (pH adjusted to 6.8-7.8) that contained Cremophor RH, Ascorbyl Palmitate, Glutamic Acid, Serine, Phenylalanine, Aspartic Acid, Threonine, Leucine, Lysine, and Isoleucine was added to a beaker containing a stir bar. Weighed amounts of 1% (w/w) Sodium Hyaluronate solution (pH adjusted to 6.8-7.8), 10% (w/w) Poloxamer 407 solution, 5% (w/w) Povidone K-90 solution (pH adjusted to 6.8-7.8), Trisodium Citrate and dextrose were added in order and with agitation. The pH of the stock solutions was adjusted so that the final product pH ranged from 6.8 to 7.8. The ingredients were stirred until it appeared that the product was in solution. Distilled water was added to bring the final batch weight to target weight.

Example 14

Test Formulation TotNut-1

| Ingredient | Percent (w/w) |
| --- | --- |
| Castor Oil | 0.15% |
| Cremophor RH | 1% |
| Poloxamer 407 | 2% |
| Carbomer Copolymer Type B | 0.005% |
| Povidone K-90 | 1.25% |
| Sodium Hyaluronate | 0.1% |
| Ascorbic Acid | 0.03% |
| Trisodium Citrate | 0.55% |
| Glutamic Acid | 0.084% |
| Serine | 0.061% |
| Phenylalanine | 0.037% |
| Aspartic Acid | 0.03% |
| Threonine | 0.028% |
| Leucine | 0.022% |
| Lysine | 0.014% |
| Dextrose | 3% |
| Tromethamine | Sufficient quantity to adjust product pH from 6.8 to 7.8 |
| Hydrochloric Acid | Sufficient quantity to adjust product pH from 6.8 to 7.8 |
| Distilled Water | Sufficient quantity to adjust batch weight to 100% of target |

Weighed amounts of Castor Oil was added to weighed amounts of Cremophor RH in a beaker containing a stir bar and mixed until clear. Poloxamer 407 was added and mixed until clear. Weighed amounts of 0.5% (w/w) Carbomer Copolymer Type B solution and 5% (w/w) Povidone K-90 solution were added and the ingredients were mixed until clear. A weighed amount of an appropriate concentration adjusted stock solution (pH adjusted to 6.8-7.8) that contains Ascorbic Acid, Glutamic Acid, Serine, Phenylalanine, Aspartic Acid, Threonine, Leucine, and Lysine was added and mixed until clear. Weighed amounts of 1% (w/w) Sodium Hyaluronate solution (pH adjusted to 6.8-7.8), Trisodium Citrate, and dextrose were added in order and with agitation. The pH of the stock solutions was adjusted so that the final product pH ranged from 6.8 to 7.8. The ingredients were stirred until it appears that the product is in solution (microemulsion). Distilled water was added to bring the final batch weight to target weight.

Example 15

Test Formulation TotNut-2

| Ingredient | Percent (w/w) |
| --- | --- |
| Flaxseed Oil | 0.15% |
| Cremophor RH | 1% |
| Poloxamer 407 | 2% |
| Carbomer Copolymer Type B | 0.005% |
| Povidone K-90 | 1.25% |
| Sodium Hyaluronate | 0.1% |
| Ascorbic Acid | 0.03% |
| Trisodium Citrate | 0.55% |
| Glutamic Acid | 0.084% |
| Serine | 0.061% |
| Phenylalanine | 0.037% |
| Aspartic Acid | 0.03% |
| Threonine | 0.028% |
| Leucine | 0.022% |
| Lysine | 0.014% |
| Dextrose | 3% |
| Tromethamine | Sufficient quantity to adjust product pH from 6.8 to 7.8 |
| Hydrochloric Acid | Sufficient quantity to adjust product pH from 6.8 to 7.8 |
| Distilled Water | Sufficient quantity to adjust batch weight to 100% of target |

Weighed amounts of Flaxseed Oil was added to weighed amounts of Cremophor RH in a beaker containing a stir bar and mixed until clear. Poloxamer 407 was added and mixed until clear. Weighed amounts of 0.5% (w/w) Carbomer Copolymer Type B solution and 5% (w/w) Povidone K-90 solution were added and the ingredients were mixed until clear. A weighed amount of an appropriate concentration adjusted (pH adjusted to 6.8-7.8) stock solution that contains Ascorbic Acid, Glutamic Acid, Serine, Phenylalanine, Aspartic Acid, Threonine, Leucine, and Lysine was added and mixed until clear. Weighed amounts of 1% (w/w) Sodium Hyaluronate solution (pH adjusted to 6.8-7.8), Trisodium Citrate, and dextrose were added in order and with agitation. The pH of the stock solutions was preadjusted so that the final product pH ranged from 6.8 to 7.8. The ingredients were stirred until it appeared that the product was in solution (microemulsion). Distilled water is added to bring the final batch weight to target weight.

Example 16

Test Formulation TotNut-3

| Ingredient | Percent (w/w) |
| --- | --- |
| Sesame Seed Oil | 0.15% |
| Cremophor RH | 1% |
| Poloxamer 407 | 2% |
| Carbomer Copolymer Type B | 0.005% |

Test Formulation TotNut-3

| Ingredient | Percent (w/w) |
| --- | --- |
| Povidone K-90 | 1.25% |
| Sodium Hyaluronate | 0.1% |
| Ascorbic Acid | 0.03% |
| Trisodium Citrate | 0.55% |
| Glutamic Acid | 0.084% |
| Serine | 0.061% |
| Phenylalanine | 0.037% |
| Aspartic Acid | 0.03% |
| Threonine | 0.028% |
| Leucine | 0.022% |
| Lysine | 0.014% |
| Dextrose | 3% |
| Tromethamine | Sufficient quantity to adjust product pH from 6.8 to 7.8 |
| Hydrochloric Acid | Sufficient quantity to adjust product pH from 6.8 to 7.8 |
| Distilled Water | Sufficient quantity to adjust batch weight to 100% of target |

A weighed amount of Sesame Seed Oil was added to a weighed amount of Cremophor RH in a beaker containing a stir bar and mixed until clear. Poloxamer 407 was added and mixed until clear. Weighed amounts of 0.5% (w/w) Carbomer Copolymer Type B solution and 5% (w/w) Povidone K-90 solution were added and the ingredients were mixed until clear. A weighed amount of an appropriate concentration adjusted (pH adjusted to 6.8-7.8) stock solution that contains Ascorbic Acid, Glutamic Acid, Serine, Phenylalanine, Aspartic Acid, Threonine, Leucine, and Lysine was added and mixed until clear. Weighed amounts of 1% (w/w) Sodium Hyaluronate solution (pH adjusted to 6.8-7.8), Trisodium Citrate, and Dextrose were added in order and with agitation. The pH of the stock solutions was preadjusted so that the final product pH ranged from 6.8 to 7.8. The ingredients were stirred until it appeared that the product was in solution (microemulsion). Distilled water was added to bring the final batch weight to target weight.

Example 17

Test Formulation TotNut-4

| Ingredient | Percent (w/w) |
| --- | --- |
| Sea Buckthorn Seed Oil | 0.15% |
| Cremophor RH | 1% |
| Poloxamer 407 | 2% |
| Carbomer Copolymer Type B | 0.005% |
| Povidone K-90 | 1.25% |
| Sodium Hyaluronate | 0.1% |
| Ascorbic Acid | 0.03% |
| Trisodium Citrate | 0.55% |
| Glutamic Acid | 0.084% |
| Serine | 0.061% |
| Phenylalanine | 0.037% |
| Aspartic Acid | 0.03% |
| Threonine | 0.028% |
| Leucine | 0.022% |
| Lysine | 0.014% |
| Dextrose | 3% |
| Tromethamine | Sufficient quantity to adjust product pH from 6.8 to 7.8 |
| Hydrochloric Acid | Sufficient quantity to adjust product pH from 6.8 to 7.8 |
| Distilled Water | Sufficient quantity to adjust batch weight to 100% of target |

A weighed amount of Sea Buckthorn Seed Oil is added to a weighed amount of Cremophor RH in a beaker containing a stir bar and mixed until clear. A weighed amount of Poloxamer 407 was added and mixed until clear. Weighed amounts of 0.5% (w/w) Carbomer Copolymer Type B solution and 5% (w/w) Povidone K-90 solution were added and the ingredients were mixed until clear. A weighed amount of an appropriate concentration adjusted (pH adjusted to 6.8-7.8) stock solution that contains Ascorbic Acid, Glutamic Acid, Serine, Phenylalanine, Aspartic Acid, Threonine, Leucine, and Lysine were added and mixed until clear. Weighed amounts of 1% (w/w) Sodium Hyaluronate solution (pH adjusted to 6.8-7.8), Trisodium Citrate, and Dextrose were added in order and with agitation. The pH of the stock solutions was preadjusted so that the final product pH ranged from 6.8 to 7.8. The ingredients were stirred until it appeared that the product was in solution (microemulsion). Distilled water was added to bring the final batch weight to target weight.

Example 18

Test Formulation TotNut-5

| Ingredient | Percent (w/w) |
| --- | --- |
| Sea Buckthorn Pulp Oil | 0.15% |
| Cremophor RH | 1% |
| Poloxamer 407 | 2% |
| Carbomer Copolymer Type B | 0.005% |
| Povidone K-90 | 1.25% |
| Sodium Hyaluronate | 0.1% |
| Ascorbic Acid | 0.03% |
| Trisodium Citrate | 0.55% |
| Glutamic Acid | 0.084% |
| Serine | 0.061% |
| Phenylalanine | 0.037% |
| Aspartic Acid | 0.03% |
| Threonine | 0.028% |
| Leucine | 0.022% |
| Lysine | 0.014% |
| Dextrose | 3% |
| Tromethamine | Sufficient quantity to adjust product pH from 6.8 to 7.8 |
| Hydrochloric Acid | Sufficient quantity to adjust product pH from 6.8 to 7.8 |
| Distilled Water | Sufficient quantity to adjust batch weight to 100% of target |

A weighed amount of Sea Buckthorn Pulp Oil was added to a weighed amount of Cremophor RH in a beaker containing a stir bar and mixed until clear. Poloxamer 407 was added and mixed until clear. Weighed amounts of 0.5% (w/w) Carbomer Copolymer Type B solution and 5% (w/w) Povidone K-90 solution were added and the ingredients were mixed until clear. A weighed amount of an appropriate concentration stock solution (pH adjusted to 6.8-7.8) that contained Ascorbic Acid, Glutamic Acid, Serine, Phenylalanine, Aspartic Acid, Threonine, Leucine, and Lysine was added and mixed until clear. Weighed amounts of 1% (w/w) Sodium Hyaluronate solution (pH adjusted to 6.8-7.8), Trisodium Citrate, and Dextrose were added in order and with agitation. The pH of the stock solutions was preadjusted so that the final product pH ranged from 6.8 to 7.8. The ingredients were stirred until it appeared that the product was in solution (microemulsion). Distilled water is added to bring the final batch weight to target weight.

Example 19

| Test Formulation TotNut-6 | |
|---|---|
| Ingredient | Percent (w/w) |
| Perilla Seed Oil | 0.15% |
| Cremophor RH | 1% |
| Poloxamer 407 | 2% |
| Carbomer Copolymer Type B | 0.005% |
| Povidone K-90 | 1.25% |
| Sodium Hyaluronate | 0.1% |
| Ascorbic Acid | 0.03% |
| Trisodium Citrate | 0.55% |
| Glutamic Acid | 0.084% |
| Serine | 0.061% |
| Phenylalanine | 0.037% |
| Aspartic Acid | 0.03% |
| Threonine | 0.028% |
| Leucine | 0.022% |
| Lysine | 0.014% |
| Dextrose | 3% |
| Tromethamine | Sufficient quantity to adjust product pH from 6.8 to 7.8 |
| Hydrochloric Acid | Sufficient quantity to adjust product pH from 6.8 to 7.8 |
| Distilled Water | Sufficient quantity to adjust batch weight to 100% of target |

A weighed amount of Perilla Seed Oil was added to a weighed amount of Cremophor RH in a beaker containing a stir bar and mixed until clear. Poloxamer 407 was added and mixed until clear. Weighed amounts of 0.5% (w/w) Carbomer Copolymer Type B solution and 5% (w/w) Povidone K-90 solution were added and the ingredients were mixed until clear. A weighed amount of an appropriate concentration adjusted (pH adjusted to 6.8-7.8) stock solution that contained Ascorbic Acid, Glutamic Acid, Serine, Phenylalanine, Aspartic Acid, Threonine, Leucine, and Lysine was added and mixed until clear. Weighed amounts of 1% (w/w) Sodium Hyaluronate solution (pH adjusted to 6.8-7.8), Trisodium Citrate, and Dextrose were added in order and with agitation. The pH of the stock solutions was preadjusted so that the final product pH ranged from 6.8 to 7.8. The ingredients were stirred until it appeared that the product was in solution (microemulsion). Distilled water is added to bring the final batch weight to target weight.

Example 20

| Test Formulation TotNut-7 | |
|---|---|
| Ingredient | Percent (w/w) |
| Rosehip Seed Oil | 0.15% |
| Cremophor RH | 1% |
| Poloxamer 407 | 2% |
| Carbomer Copolymer Type B | 0.005% |
| Povidone K-90 | 1.25% |
| Sodium Hyaluronate | 0.1% |
| Ascorbic Acid | 0.03% |
| Trisodium Citrate | 0.55% |
| Glutamic Acid | 0.084% |
| Serine | 0.061% |
| Phenylalanine | 0.037% |
| Aspartic Acid | 0.03% |
| Threonine | 0.028% |
| Leucine | 0.022% |
| Lysine | 0.014% |
| Dextrose | 3% |
| Tromethamine | Sufficient quantity to adjust product pH from 6.8 to 7.8 |
| Hydrochloric Acid | Sufficient quantity to adjust product pH from 6.8 to 7.8 |
| Distilled Water | Sufficient quantity to adjust batch weight to 100% of target |

A weighed amount of Rosehip Seed Oil was added to a weighed amount of Cremophor RH in a beaker containing a stir bar and mixed until clear. Poloxamer 407 was added and mixed until clear. Weighed amounts of 0.5% (w/w) Carbomer Copolymer Type B solution and 5% (w/w) Povidone K-90 solution were added and the ingredients were mixed until clear. A weighed amount of an appropriate concentration adjusted (pH adjusted to 6.8-7.8) stock solution that contained Ascorbic Acid, Glutamic Acid, Serine, Phenylalanine, Aspartic Acid, Threonine, Leucine, and Lysine was added and mixed until clear. Weighed amounts of 1% (w/w) Sodium Hyaluronate solution (pH adjusted to 6.8-7.8), Trisodium Citrate, and Dextrose were added in order and with agitation. The pH of the stock solutions was preadjusted so that the final product pH ranged from 6.8 to 7.8. The ingredients were stirred until it appeared that the product was in solution (microemulsion). Distilled water was added to bring the final batch weight to target weight.

Example 21

| Test Formulation TotNut-8 | |
|---|---|
| Ingredient | Percent (w/w) |
| Pecan Nut Oil | 0.15% |
| Cremophor RH | 1% |
| Poloxamer 407 | 2% |
| Carbomer Copolymer Type B | 0.005% |
| Povidone K-90 | 1.25% |
| Sodium Hyaluronate | 0.1% |
| Ascorbic Acid | 0.03% |
| Trisodium Citrate | 0.55% |
| Glutamic Acid | 0.084% |
| Serine | 0.061% |
| Phenylalanine | 0.037% |
| Aspartic Acid | 0.03% |
| Threonine | 0.028% |
| Leucine | 0.022% |
| Lysine | 0.014% |
| Dextrose | 3% |
| Tromethamine | Sufficient quantity to adjust product pH from 6.8 to 7.8 |
| Hydrochloric Acid | Sufficient quantity to adjust product pH from 6.8 to 7.8 |
| Distilled Water | Sufficient quantity to adjust batch weight to 100% of target |

A weighed amount of Pecan Nut Oil was added to a weighed amount of Cremophor RH in a beaker containing a stir bar and mixed until clear. Poloxamer 407 was added and mixed until clear. Weighed amounts of 0.5% (w/w) Carbomer Copolymer Type B solution and 5% (w/w) Povidone K-90 solution were added and the ingredients were mixed until clear. A weighed amount of an appropriate concentration adjusted (pH adjusted to 6.8-7.8) stock solution that contained Ascorbic Acid, Glutamic Acid, Serine, Phenylalanine, Aspartic Acid, Threonine, Leucine, and Lysine was added and mixed until clear. Weighed amounts of 1% (w/w) Sodium Hyaluronate (pH adjusted to 6.8-7.8), Trisodium Citrate, and Dextrose were added in order and with agitation. The pH of the stock solutions was preadjusted so that the final product pH ranged from 6.8 to 7.8. The ingredients were stirred until it appeared that the product was in solution (microemulsion). Distilled water was added to bring the final batch weight to target weight.

Example 22

Test Formulation TotNut-9

| Ingredient | Percent (w/w) |
|---|---|
| Macadamia Nut Oil | 0.15% |
| Cremophor RH | 1% |
| Poloxamer 407 | 2% |
| Carbomer Copolymer Type B | 0.005% |
| Povidone K-90 | 1.25% |
| Sodium Hyaluronate | 0.1% |
| Ascorbic Acid | 0.03% |
| Trisodium Citrate | 0.55% |
| Glutamic Acid | 0.084% |
| Serine | 0.061% |
| Phenylalanine | 0.037% |
| Aspartic Acid | 0.03% |
| Threonine | 0.028% |
| Leucine | 0.022% |
| Lysine | 0.014% |
| Dextrose | 3% |
| Tromethamine | Sufficient quantity to adjust product pH from 6.8 to 7.8 |
| Hydrochloric Acid | Sufficient quantity to adjust product pH from 6.8 to 7.8 |
| Distilled Water | Sufficient quantity to adjust batch weight to 100% of target |

A weighed amount of Macadamia Nut Oil was added to a weighed amount of Cremophor RH in a beaker containing a stir bar and mixed until clear. Poloxamer 407 was added and mixed until clear. Weighed amounts of 0.5% (w/w) Carbomer Copolymer Type B solution and 5% (w/w) Povidone K-90 solution were added and the ingredients were mixed until clear. A weighed amount of an appropriate concentration adjusted (pH adjusted to 6.8-7.8) stock solution that contained Ascorbic Acid, Glutamic Acid, Serine, Phenylalanine, Aspartic Acid, Threonine, Leucine, and Lysine was added and mixed until clear. Weighed amounts of 1% (w/w) Sodium Hyaluronate solution (pH adjusted to 6.8-7.8), Trisodium Citrate, and Dextrose were added in order and with agitation. The pH of the stock solutions was preadjusted so that the final product pH ranges from 6.8 to 7.8. The ingredients were stirred until it appeared that the product was in solution (microemulsion). Distilled water was added to bring the final batch weight to target weight.

Example 23

Test Formulation Osmot-1

| Ingredient | Percent (w/w) |
|---|---|
| Castor Oil | 0.15% |
| Cremophor RH | 1% |
| Poloxamer 407 | 2% |
| Carbomer Copolymer Type B | 0.005% |
| Povidone K-90 | 1.25% |
| Sodium Hyaluronate | 0.1% |
| Ascorbic Acid | 0.03% |
| Trisodium Citrate | 0.55% |
| Glutamic Acid | 0.084% |
| Serine | 0.061% |
| Phenylalanine | 0.037% |
| Aspartic Acid | 0.03% |
| Threonine | 0.028% |
| Leucine | 0.022% |
| Lysine | 0.014% |
| Proline | 0.1% |
| Dextrose | 3% |
| Tromethamine | Sufficient quantity to adjust product pH from 6.8 to 7.8 |
| Hydrochloric Acid | Sufficient quantity to adjust product pH from 6.8 to 7.8 |
| Distilled Water | Sufficient quantity to adjust batch weight to 100% of target |

A weighed amounts of Castor Oil was added to a weighed amount of Cremophor RH in a beaker containing a stir bar and was mixed until clear. Poloxamer 407 was added and mixed until clear. Weighed amounts of 0.5% (w/w) Carbomer Copolymer Type B solution (pH adjusted to 6.8-7.8) and 5% (w/w) Povidone K-90 solution (pH adjusted to 6.8-7.8) were added and the ingredients were mixed until clear. A weighed amount of an appropriate concentration adjusted (pH adjusted to 6.8-7.8) stock solution that contained Ascorbic Acid, Glutamic Acid, Serine, Phenylalanine, Aspartic Acid, Threonine, Leucine, Lysine, and Proline was added and mixed until clear. Weighed amounts of 1% (w/w) Sodium Hyaluronate solution (pH adjusted to 6.8-7.8), Trisodium Citrate, and Dextrose were added in order and with agitation. The pH of the stock solutions was preadjusted so that the final product pH ranged from 6.8 to 7.8. The ingredients were stirred until it appeared that the product was in solution (microemulsion). Distilled water was added to bring the final batch weight to target weight.

Example 24

Test Formulation Osmot-3

| Ingredient | Percent (w/w) |
|---|---|
| Castor Oil | 0.15% |
| Cremophor RH | 1% |
| Poloxamer 407 | 2% |
| Carbomer Copolymer Type B | 0.005% |
| Povidone K-90 | 1.25% |
| Sodium Hyaluronate | 0.1% |
| Ascorbic Acid | 0.03% |
| Trisodium Citrate | 0.55% |
| Glutamic Acid | 0.084% |
| Serine | 0.061% |
| Phenylalanine | 0.037% |
| Aspartic Acid | 0.03% |
| Threonine | 0.028% |
| Leucine | 0.022% |
| Lysine | 0.014% |
| Betaine | 0.2% |
| Dextrose | 3% |
| Tromethamine | Sufficient quantity to adjust product pH from 6.8 to 7.8 |
| Hydrochloric Acid | Sufficient quantity to adjust product pH from 6.8 to 7.8 |
| Distilled Water | Sufficient quantity to adjust batch weight to 100% of target |

A weighed amount of Castor Oil was added to a weighed amount of Cremophor RH in a beaker containing a stir bar and was mixed until clear. Poloxamer 407 was added and mixed until clear. Weighed amounts of 0.5% (w/w) Carbomer Copolymer Type B solution (pH adjusted to 6.8-7.8) and 5% (w/w) Povidone K-90 solution (pH adjusted to 6.8-7.8) were added and the ingredients were mixed until clear. A weighed amount of an appropriate concentration stock solution (pH adjusted to 6.8-7.8) that contained Ascorbic Acid, Glutamic Acid, Serine, Phenylalanine, Aspartic Acid, Threonine, Leucine, Lysine, and Betaine was added and mixed until clear. Weighed amounts of 1% (w/w) Sodium Hyaluronate solution (pH adjusted to 6.8-7.8), Trisodium Citrate, and Dextrose are added in order and with agitation. The pH of the stock solutions was preadjusted so that the final product pH ranges from 6.8 to 7.8. The ingredients were stirred until it appeared that the product was clear. Distilled water was added to bring the final batch weight to target weight.

Example 25

Test Formulation Osmot-4

| Ingredient | Percent (w/w) |
|---|---|
| Castor Oil | 0.15% |
| Cremophor RH | 1% |
| Poloxamer 407 | 2% |
| Carbomer Copolymer Type B | 0.005% |
| Povidone K-90 | 1.25% |
| Sodium Hyaluronate | 0.1% |
| Ascorbic Acid | 0.03% |
| Trisodium Citrate | 0.55% |
| Glutamic Acid | 0.084% |
| Serine | 0.061% |
| Phenylalanine | 0.037% |
| Aspartic Acid | 0.03% |
| Threonine | 0.028% |
| Leucine | 0.022% |
| Lysine | 0.014% |
| Inositol | 0.35% |
| Dextrose | 3% |
| Tromethamine | Sufficient quantity to adjust product pH from 6.8 to 7.8 |
| Hydrochloric Acid | Sufficient quantity to adjust product pH from 6.8 to 7.8 |
| Distilled Water | Sufficient quantity to adjust batch weight to 100% of target |

A weighed amounts of Castor Oil was added to a weighed amount of Cremophor RH in a beaker containing a stir bar and mixed until clear. Poloxamer 407 was added and mixed until clear. Weighed amounts of 0.5% (w/w) Carbomer Copolymer Type B solution and 5% (w/w) Povidone K-90 solution were added and the ingredients were mixed until clear. A weighed amount of an appropriate concentration adjusted (pH adjusted to 6.8 to 7.8) stock solution that contains Ascorbic Acid, Glutamic Acid, Serine, Phenylalanine, Aspartic Acid, Threonine, Leucine, Lysine, and Inositol was added and mixed until clear. Weighed amounts of Sodium Hyaluronate, Trisodium Citrate, and Dextrose were added in order and with agitation. The pH of the stock solutions was preadjusted so that the final product pH ranged from 6.8 to 7.8. The ingredients were stirred until it appeared that the product was in solution (microemulsion). Distilled water was added to bring the final batch weight to target weight.

Example 26

Test Formulation Osmot-6

| Ingredient | Percent (w/w) |
|---|---|
| Castor Oil | 0.15% |
| Cremophor RH | 1% |
| Poloxamer 407 | 2% |
| Carbomer Copolymer Type B | 0.005% |
| Povidone K-90 | 1.25% |
| Sodium Hyaluronate | 0.1% |
| Ascorbic Acid | 0.03% |
| Trisodium Citrate | 0.55% |
| Glutamic Acid | 0.084% |
| Serine | 0.061% |
| Phenylalanine | 0.037% |
| Aspartic Acid | 0.03% |
| Threonine | 0.028% |
| Leucine | 0.022% |
| Lysine | 0.014% |
| Trehalose | 3% |
| Dextrose | 1% |
| Tromethamine | Sufficient quantity to adjust product pH from 6.8 to 7.8 |
| Hydrochloric Acid | Sufficient quantity to adjust product pH from 6.8 to 7.8 |
| Distilled Water | Sufficient quantity to adjust batch weight to 100% of target |

A weighed amounts of Castor Oil was added to a weighed amount of Cremophor RH in a beaker containing a stir bar and mixed until clear. Poloxamer 407 was added and mixed until clear. Weighed amounts of Carbomer Copolymer Type B solution and Povidone K-90 solution were added and the ingredients were mixed until clear. A weighed amount of an appropriate concentration adjusted (pH adjusted (pH adjusted to 6.8-7.8)) stock solution that contains Ascorbic Acid, Glutamic Acid, Serine, Phenylalanine, Aspartic Acid, Threonine, Leucine, Lysine, and Trehalose was added and mixed until clear. Weighed amounts of Sodium Hyaluronate, Trisodium Citrate, and Dextrose were added in order and with agitation. The pH of the stock solutions were preadjusted so that the final product pH ranged from 6.8 to 7.8. The ingredients were stirred until it appeared that the product was in solution (microemulsion). Distilled water was added to bring the final batch weight to target weight.

Example 27

Test Formulation Osmot-7

| Ingredient | Percent (w/w) |
|---|---|
| Castor Oil | 0.15% |
| Cremophor RH | 1% |
| Poloxamer 407 | 2% |
| Carbomer Copolymer Type B | 0.005% |
| Povidone K-90 | 1.25% |
| Sodium Hyaluronate | 0.1% |
| Ascorbic Acid | 0.03% |
| Trisodium Citrate | 0.55% |
| Glutamic Acid | 0.084% |
| Serine | 0.061% |
| Phenylalanine | 0.037% |
| Aspartic Acid | 0.03% |
| Threonine | 0.028% |
| Leucine | 0.022% |
| Lysine | 0.014% |
| Taurine | 0.125% |
| Dextrose | 2% |

-continued

| Test Formulation Osmot-7 | |
|---|---|
| Ingredient | Percent (w/w) |
| Tromethamine | Sufficient quantity to adjust product pH from 6.8 to 7.8 |
| Hydrochloric Acid | Sufficient quantity to adjust product pH from 6.8 to 7.8 |
| Distilled Water | Sufficient quantity to adjust batch weight to 100% of target |

A weighed amounts of Castor Oil was added to a weighed amounts of Cremophor RH in a beaker containing a stir bar and mixed until clear. Poloxamer 407 was added and mixed until clear. Weighed amounts of 0.5% (w/w) Carbomer Copolymer Type B solution and 5% (w/w) Povidone K-90 solution were added and the ingredients were mixed until clear. A weighed amount of an appropriate concentration adjusted (pH adjusted (pH adjusted to 6.8-7.8) stock solution that contained Ascorbic Acid, Glutamic Acid, Serine, Phenylalanine, Aspartic Acid, Threonine, Leucine, Lysine, and Taurine was added and mixed until clear. Weighed amounts of 1% (w/w) Sodium Hyaluronate, Trisodium Citrate, and Dextrose were added in order and with agitation. The pH of the stock solutions was preadjusted so that the final product pH ranged from 6.8 to 7.8. The ingredients were stirred until it appeared that the product was in solution (microemulsion). Distilled water was added to bring the final batch weight to target weight.

Example 28

| Test Formulation ES-1 | |
|---|---|
| Ingredient | Percent (w/w) |
| Tocopherol (Sunflower Lecithin, Tocomix ™ 70R) | 0.002% |
| Anchovy Oil, (Provinal ®) | 0.15% |
| Cremophor EL | 4% |
| Poloxamer 407 | 2% |
| Povidone K-90 | 1.25% |
| Sodium Hyaluronate | 0.1% |
| Carbomer Copolymer Type B | 0.005% |
| Ascorbic Acid | 0.1% |
| Trisodium Citrate | 0.45% |
| Sorbitol | 3.3% |
| Tromethamine | Sufficient quantity to adjust product pH from 6.8 to 7.8 |
| Hydrochloric Acid | Sufficient quantity to adjust product pH from 6.8 to 7.8 |
| Distilled Water | Sufficient quantity to adjust batch weight to 100% of target |

A weighed amount of Tocopherol (Tocomix™ 70R) was added to a weighed amount of Anchovy Oil and mixed until clear. A weighed amount of Tocopherol and Anchovy Oil solution was added to a weighed amount of Cremophor EL in a beaker containing a stir bar and mixed until clear. A weighed amount of Poloxamer 407, Carbomer Copolymer Type B, Povidone K-90, and Sodium Hyaluronate stock solution (pH adjusted to 6.8-7.8) was added, and the ingredients were mixed until clear. A weighed amount of an Ascorbic Acid, Trisodium Citrate, and Sorbitol pH adjusted (6.8-7.8) stock solution was added, and the ingredients were mixed until clear. The pH of the stock solutions was preadjusted so that the final product pH ranged from 6.8 to 7.8. Distilled water was added to bring the final batch weight to target weight.

Example 29

| Test Formulation ES-2 | |
|---|---|
| Ingredient | Percent (w/w) |
| Tocopherol (Sunflower Lecithin, Tocomix ™ 70R) | 0.002% |
| Perilla Oil | 0.15% |
| Cremophor EL | 4% |
| Poloxamer 407 | 2% |
| Povidone K-90 | 1.25% |
| Sodium Hyaluronate | 0.1% |
| Carbomer Copolymer Type B | 0.005% |
| Ascorbic Acid | 0.1% |
| Trisodium Citrate | 0.45% |
| Sorbitol | 3.3% |
| Tromethamine | Sufficient quantity to adjust product pH from 6.8 to 7.8 |
| Hydrochloric Acid | Sufficient quantity to adjust product pH from 6.8 to 7.8 |
| Distilled Water | Sufficient quantity to adjust batch weight to 100% of target |

A weighed amount of Tocopherol (Tocomix™ 70R) was added to a weighed amount of Perilla Oil and mixed until clear. A weighed amount of Tocopherol/Perilla Oil solution was added to a weighed amount of Cremophor EL in a beaker containing a stir bar and mixed until clear. A weighed amount of Poloxamer 407, Carbomer Copolymer Type B, Povidone K-90, and Sodium Hyaluronate pH adjusted (6.8-7.8) stock solution was added, and the ingredients were mixed until clear. A weighed amount of an Ascorbic Acid, Trisodium Citrate, and Sorbitol pH adjusted (6.8-7.8) stock solution was added, and the ingredients were mixed until clear. The pH of the stock solutions was preadjusted so that the final product pH ranged from 6.8 to 7.8. Distilled water was added to bring the final batch weight to target weight.

Example 30

| Test Formulation ES-3 | |
|---|---|
| Ingredient | Percent (w/w) |
| Tocopherol (Sunflower Lecithin, Tocomix ™ 70R) | 0.002% |
| Castor Oil | 0.15% |
| Cremophor EL | 4% |
| Poloxamer 407 | 2% |
| Povidone K-90 | 1.25% |
| Sodium Hyaluronate | 0.1% |
| Carbomer Copolymer Type B | 0.005% |
| Ascorbic Acid | 0.1% |
| Trisodium Citrate | 0.45% |
| Sorbitol | 3.3% |
| Tromethamine | Sufficient quantity to adjust product pH from 6.8 to 7.8 |
| Hydrochloric Acid | Sufficient quantity to adjust product pH from 6.8 to 7.8 |
| Distilled Water | Sufficient quantity to adjust batch weight to 100% of target |

A weighed amount of Tocopherol (Tocomix™ 70R) was added to a weighed amount of Castor Oil and mixed until clear. A weighed amount of Tocopherol/Castor Oil solution was added to a weighed amount of Cremophor EL in a beaker containing a stir bar and mixed until clear. A weighed amount of Poloxamer 407, Carbomer Copolymer Type B, Povidone K-90, and Sodium Hyaluronate pH adjusted (6.8-7.8) stock solution was added, and the ingredients were mixed until clear. A weighed amount of an Ascorbic Acid, Trisodium Citrate, and Sorbitol pH adjusted (6.8-7.8) stock solution was added, and the ingredients were mixed until clear. The pH of the stock solutions was preadjusted so that the final product pH ranged from 6.8 to 7.8. Distilled water was added to bring the final batch weight to target weight.

Example 31

| Test Formulation ES-4 | |
|---|---|
| Ingredient | Percent (w/w) |
| Alpha-Tocopherol | 0.002% |
| Anchovy Oil, (Provinal ®) | 0.15% |
| Cremophor EL | 4% |
| Poloxamer 407 | 2% |
| Povidone K-90 | 1.25% |
| Sodium Hyaluronate | 0.1% |
| Carbomer Copolymer Type B | 0.005% |
| Ascorbic Acid | 0.1% |
| Trisodium Citrate | 0.45% |
| Sorbitol | 3.3% |
| Tromethamine | Sufficient quantity to adjust product pH from 6.8 to 7.8 |
| Hydrochloric Acid | Sufficient quantity to adjust product pH from 6.8 to 7.8 |
| Distilled Water | Sufficient quantity to adjust batch weight to 100% of target |

A weighed amount of Tocopherol (Tocomix™ 70R) was added to a weighed amount of Anchovy Oil and mixed until clear. A weighed amount of Alpha-tocopherol and Anchovy oil solution was added to a weighed amount of Cremophor EL in a beaker containing a stir bar and mixed until clear. A weighed amount of Poloxamer 407, Carbomer Copolymer Type B, Povidone K-90, and Sodium Hyaluronate stock solution (pH adjusted to 6.8-7.8) was added, and the ingredients were mixed until clear. A weighed amount of an Ascorbic Acid, Trisodium Citrate, and Sorbitol stock solution (pH adjusted to 6.8-7.8) was added, and the ingredients were mixed until clear. The pH of the stock solutions was preadjusted so that the final product pH ranged from 6.8 to 7.8. Distilled water was added to bring the final batch weight to target weight.

Example 32

| Test Formulation ES-6 | |
|---|---|
| Ingredient | Percent (w/w) |
| Castor Oil | 0.15% |
| Cremophor EL | 4% |
| Poloxamer 407 | 2% |
| Povidone K-90 | 1.25% |
| Sodium Hyaluronate | 0.1% |
| Carbomer Copolymer Type B | 0.005% |
| Sorbitol | 4.5% |
| Tromethamine | Sufficient quantity to adjust product pH from 6.8 to 7.8 |
| Hydrochloric Acid | Sufficient quantity to adjust product pH from 6.8 to 7.8 |
| Distilled Water | Sufficient quantity to adjust batch weight to 100% of target |

A weighed amount of Castor Oil was added to a weighed amount of Cremophor EL in a beaker containing a stir bar and mixed until clear. A weighed amount of Poloxamer 407, Carbomer Copolymer Type B, Povidone K-90, and Sodium Hyaluronate stock solution (pH adjusted to 6.8-7.8) was added, and the ingredients were mixed until clear. A weighed amount of Sorbitol was added to the emulsion, and the ingredients were mixed until clear. The pH of the solution was adjusted so that the final product pH ranged from 6.8 to 7.8. Distilled water was added to bring the final batch weight to target weight.

Example 33

| Test Formulation ES-7 | |
|---|---|
| Ingredient | Percent (w/w) |
| Tocopherol (Sunflower Lecithin, Tocomix ™ 70R) | 0.002% |
| Anchovy Oil, (Provinal ®) | 0.15% |
| Cremophor EL | 4% |
| Poloxamer 407 | 2% |
| Povidone K-90 | 1.25% |
| Carbomer Copolymer Type B | 0.005% |
| Sodium Hyaluronate | 0.1% |
| Ascorbic Acid | 0.1% |
| Trisodium Citrate | 0.45% |
| Glutamic Acid | 0.084% |
| Serine | 0.061% |
| Phenylalanine | 0.037% |
| Aspartic Acid | 0.03% |
| Threonine | 0.028% |
| Leucine | 0.022% |
| Lysine | 0.014% |
| Betaine | 0.2% |
| Sorbitol | 2.2% |
| Tromethamine | Sufficient quantity to adjust product pH from 6.8 to 7.8 |
| Hydrochloric Acid | Sufficient quantity to adjust product pH from 6.8 to 7.8 |
| Distilled Water | Sufficient quantity to adjust batch weight to 100% of target |

A weighed amount of Tocopherol (Tocomix™ 70R) was added to a weighed amount of Anchovy Oil and mixed until clear. A weighed amount of the Tocopherol and Anchovy Oil solution was added to a weighed amount of Cremophor EL in a beaker containing a stir bar and mixed until clear. A weighed amount of Poloxamer 407, Carbomer Copolymer Type B, Povidone K-90, and Sodium Hyaluronate stock solution (pH adjusted to 6.8-7.8) was added, and the ingredients were mixed until clear. A weighed amount of an appropriate concentration adjusted stock solution (pH adjusted to 6.8-7.8) that contains Glutamic Acid, Serine, Phenylalanine, Aspartic Acid, Threonine, Leucine, and Lysine was added to the emulsion and mixed until clear. Weighed amounts of Ascorbic Acid, Trisodium Citrate, Sorbitol, and Betaine were added, and the ingredients were mixed until clear. The pH of the solution was adjusted so that the final product pH ranged from 6.8 to 7.8. Distilled water was added to bring the final batch weight to target weight.

Example 34

| Test Formulation ES-8 | |
|---|---|
| Ingredient | Percent (w/w) |
| Tocopherol (Sunflower Lecithin, Tocomix™ 70R) | 0.002% |
| Anchovy Oil, (Provinal ®) | 0.15% |
| Cremophor EL | 4% |
| Poloxamer 407 | 2% |
| Povidone K-90 | 1.25% |
| Sodium Hyaluronate | 0.1% |
| Carbomer Copolymer Type B | 0.005% |
| Ascorbic Acid | 0.1% |
| Trisodium Citrate | 0.45% |
| Ferulic acid | 0.02% |
| Sorbitol | 3.3% |
| Tromethamine | Sufficient quantity to adjust product pH from 6.8 to 7.8 |
| Hydrochloric Acid | Sufficient quantity to adjust product pH from 6.8 to 7.8 |
| Distilled Water | Sufficient quantity to adjust batch weight to 100% of target |

A weighed amount of Tocopherol (Tocomix™ 70R) was added to a weighed amount of Anchovy Oil and mixed until clear. A weighed amount of the Tocopherol and Anchovy Oil solution was added to a weighed amount of Cremophor EL in a beaker containing a stir bar and mixed until clear. A weighed amount of Poloxamer 407, Carbomer Copolymer Type B, Povidone K-90, and Sodium Hyaluronate stock solution (pH adjusted to 6.8-7.8) was added, and the ingredients were mixed until clear. A weighed amount of an Ascorbic Acid, Trisodium Citrate, and Sorbitol stock solution (pH adjusted to 6.8-7.8) was added, and the ingredients were mixed until clear. A weighed amount of Ferulic acid was added to the solution and mixed until clear. The pH of the solution was adjusted so that the final product pH ranged from 6.8 to 7.8. Distilled water was added to bring the final batch weight to target weight.

Example 35

| Test Formulation ES-9 | |
|---|---|
| Ingredient | Percent (w/w) |
| Tocopherol (Sunflower Lecithin, Tocomix™ 70R) | 0.002% |
| Anchovy Oil, (Provinal ®) | 0.15% |
| Cremophor RH | 1% |
| Poloxamer 407 | 2% |
| Povidone K-90 | 1.25% |
| Sodium Hyaluronate | 0.1% |
| Carbomer Copolymer Type B | 0.005% |
| Ascorbic Acid | 0.1% |
| Trisodium Citrate | 0.45% |
| Ferulic acid | 0.02% |
| Sorbitol | 3.3% |
| Tromethamine | Sufficient quantity to adjust product pH from 6.8 to 7.8 |
| Hydrochloric Acid | Sufficient quantity to adjust product pH from 6.8 to 7.8 |
| Distilled Water | Sufficient quantity to adjust batch weight to 100% of target |

A weighed amount of Tocopherol (Tocomix™ 70R) was added to a weighed amount of Anchovy Oil and mixed until clear. A weighed amount of the Tocopherol and Anchovy Oil solution was added to a weighed amount of Cremophor EL in a beaker containing a stir bar and mixed until clear. A weighed amount of Poloxamer 407, Carbomer Copolymer Type B, Povidone K-90, and Sodium Hyaluronate stock solution was added, and the ingredients were mixed until clear. Weighed amounts of Ascorbic Acid, Trisodium Citrate, Ferulic acid, and Sorbitol were added to the emulsion, and the ingredients were mixed until clear. The pH of the solution was adjusted so that the final product pH ranged from 6.8 to 7.8. Distilled water was added to bring the final batch weight to target weight.

Example 36

| Test Formulation ES-10 | |
|---|---|
| Ingredient | Percent (w/w) |
| Tocopherol (Sunflower Lecithin, Tocomix™ 70R) | 0.002% |
| Perilla Oil | 0.15% |
| Cremophor EL | 4% |
| Poloxamer 407 | 2% |
| Povidone K-90 | 1.25% |
| Sodium Hyaluronate | 0.1% |
| Carbomer Copolymer Type B | 0.005% |
| Ascorbic Acid | 0.1% |
| Trisodium Citrate | 0.45% |
| Ferulic acid | 0.02% |
| Sorbitol | 3.3% |
| Tromethamine | Sufficient quantity to adjust product pH from 6.8 to 7.8 |
| Hydrochloric Acid | Sufficient quantity to adjust product pH from 6.8 to 7.8 |
| Distilled Water | Sufficient quantity to adjust batch weight to 100% of target |

A weighed amount of Tocopherol (Tocomix™ 70R) was added to a weighed amount of Perilla Oil and mixed until clear. A weighed amount of the Tocopherol and Perilla Oil solution was added to a weighed amount of Cremophor EL in a beaker containing a stir bar and mixed until clear. A weighed amount of Poloxamer 407, Carbomer Copolymer Type B, Povidone K-90, and Sodium Hyaluronate stock solution was added, and the ingredients were mixed until clear. Weighed amounts of Ascorbic Acid, Trisodium Citrate, Ferulic acid, and Sorbitol were added to the emulsion, and the ingredients were mixed until clear. The pH of the solution was adjusted so that the final product pH ranged from 6.8 to 7.8. Distilled water was added to bring the final batch weight to target weight.

Example 37

| Test Formulation ES-11 | |
|---|---|
| Ingredient | Percent (w/w) |
| Cremophor EL | 4% |
| Poloxamer 407 | 2% |
| Povidone K-90 | 1.25% |
| Sodium Hyaluronate | 0.1% |
| Carbomer Copolymer Type B | 0.005% |
| Sorbitol | 4.5% |
| Tromethamine | Sufficient quantity to adjust product pH from 6.8 to 7.8 |
| Hydrochloric Acid | Sufficient quantity to adjust product pH from 6.8 to 7.8 |
| Distilled Water | Sufficient quantity to adjust batch weight to 100% of target |

A weighed amount of Poloxamer 407, Carbomer Copolymer Type B, Povidone K-90, and Sodium Hyaluronate stock solution was added to a weighed amount of Cremophor EL in a beaker containing a stir bar and mixed until clear. A weighed amount of Sorbitol was added, and the ingredients were mixed until clear. The pH of the stock solutions was adjusted so that the final product pH ranged from 6.8 to 7.8. Distilled water was added to bring the final batch weight to target weight.

Example 38

Test Formulation ES-12

| Ingredient | Percent (w/w) |
| --- | --- |
| Tocopherol (Sunflower Lecithin, Tocomix ™ 70R) | 0.002% |
| Chia Oil | 0.15% |
| Cremophor EL | 4% |
| Poloxamer 407 | 2% |
| Povidone K-90 | 1.25% |
| Sodium Hyaluronate | 0.1% |
| Carbomer Copolymer Type B | 0.005% |
| Ascorbic Acid | 0.1% |
| Trisodium Citrate | 0.45% |
| Ferulic acid | 0.02% |
| Sorbitol | 3.3% |
| Tromethamine | Sufficient quantity to adjust product pH from 6.8 to 7.8 |
| Hydrochloric Acid | Sufficient quantity to adjust product pH from 6.8 to 7.8 |
| Distilled Water | Sufficient quantity to adjust batch weight to 100% of target |

A weighed amount of Tocopherol (Tocomix™ 70R) was added to a weighed amount of Chia Oil and mixed until clear. A weighed amount of the Tocopherol and Chia Oil solution was added to a weighed amount of Cremophor EL in a beaker containing a stir bar and mixed until clear. A weighed amount of Poloxamer 407, Carbomer Copolymer Type B, Povidone K-90, and Sodium Hyaluronate stock solution was added, and the ingredients were mixed until clear. Weighed amounts of Ascorbic Acid, Trisodium Citrate, Ferulic acid, and Sorbitol were added to the emulsion, and the ingredients were mixed until clear. The pH of the solution was adjusted so that the final product pH ranged from 6.8 to 7.8. Distilled water was added to bring the final batch weight to target weight.

Selected test formulations were evaluated for Optical Clarity, Lubricity, and Spreadability.

Optical Clarity of Test Formulations was measured with a light transmission meter. Optical Clarity is expressed (Table 1) as Light Transmission Ratio, which is the measured percent light transmission value for the test formulation divided by the measured percent light transmission value for Simulated Tear Fluid. Simulated Tear Fluid is a clear water solution and a Light Transmission Ratio of 1.00 to 0.95 indicated that a test formulation is optically clear. Light Transmission Ratio Values of 0.95 to 0.90 are considered nearly clear and higher Light Transmission Ratio Values are considered more favorable.

Lubricity is the capacity of a test formulation for reducing friction and is of clinical importance as an eye lid moves over the cornea during an eyeblink. Lubricity was assessed by measuring the transit time (defined distance) for a "sled" as pulled by a constant force (analogous to the eye lid) moving over a surface (analogous to the cornea) that has been covered by the test material mixed with simulated tear fluid (analogous to an OTC dry eye product mixed with the eye's tear film). Lubricity is expressed as the Lubricity Ratio, which is the measured transit time for Simulated Tear Fluid divided by the transit time for the Test Formulation. The higher the Lubricity Ratio value, the more efficiently the Test Formulation reduces the friction of a moving object (e.g., eye lid) over a stationary surface such as the cornea.

Spreadability is the ability of a Test Formulation to overlay a hydrophobic surface. Spreadability was assessed by measuring the weight of test formulation needed to completely cover the surface of a polystyrene (hydrophobic) petri dish. This is analogous to the tear film covering the hydrophobic corneal surface during an eyeblink. Spreadability is expressed as the Spreading Ratio, which is the weight of Simulated Tear Fluid to cover a petri dish surface divided by the weight of Test Formulation needed to cover a petri dish surface. The higher the Spreadability Ratio value, the more easily the Test Formulation can cover a hydrophobic surface such as the cornea.

TABLE 1

Test Results for Example Formulations with Key Ingredients

| Test Formulation | Optical Clarity Expressed as Light Transmission Ratio - Higher Values indicate Greater Optical Clarity in Eye | Lubricity Expressed as Lubricity Ratio - Higher Values indicate Greater Reduction in Friction During Blink | Spreadability Expressed as Spreading Ratio - Higher Values indicate Greater Ability to Completely Cover the Cornea During Blink |
| --- | --- | --- | --- |
| SH-7 | 0.94 | 1.31 | 1.43 |
| FT-1 | 0.99 | 1.24 | 1.55 |
| FT-4 | 1.00 | 1.27 | 1.56 |
| FTCO-1 | 1.00 | 1.24 | 1.63 |
| FTCOL-1 | 0.89 | 1.33 | 1.64 |

In certain embodiments, surfactants Polyoxyl 35 castor oil (NF) (Cremophor EL), Polyoxyl 40 hydrogenated castor oil (NF) (Cremophor RH), and/or Ethylene oxide/propylene oxide copolymer (avg MW 9,760-13,200) (poloxamer 407) at tested concentrations result in microemulsions of castor oil that are optically clear. In additional embodiments, using the highest molecular weight grade of povidone (K90) resulted in a product with good lubricity character. In various embodiments, good spreadability was achieved with optically clear formulations that contain surfactants Polyoxyl 35 castor oil (NF) (Cremophor EL), Polyoxyl 40 hydrogenated castor oil (NF) (Cremophor RH), and/or Ethylene oxide/propylene oxide copolymer (avg MW 9,760-13,200) (poloxamer 407) with or without Castor Oil.

While the present subject matter has been described in detail with respect to specific exemplary embodiments and methods thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed:

1. An ophthalmic pharmaceutical formulation, comprising:
    a. a demulcent comprising povidone with a concentration in the range of between about 1% and about 3% (w/w);
    b. a surfactant selected from the group consisting of polyoxyl 40 hydrogenated castor oil at a concentration of about 1% (w/w) and polyoxyl 35 castor oil at a concentration of about 4% (w/w) and combinations thereof;
c. pecan nut oil at a concentration of about 0.15% (w/w);
d. hyaluronic acid or a salt thereof at a concentration of about 0.1% (w/w);
e. one or more antioxidants selected from the group consisting of ascorbic acid or salts thereof, ascorbyl palmitate, Vitamin E, tocopherol, ferulic acid, and trisodium citrate, and combinations thereof;
f. a tonicity agent selected from the group consisting of mannitol, sorbitol, and dextrose, and combinations thereof, in a total amount of up to about 5% (w/w);
g. carbomer copolymer type B at a concentration of about 0.005% (w/w);
h. one or more amino acids selected from the group consisting of glutamic acid, serine, phenylalanine, aspartic acid, threonine, leucine, lysine, and isoleucine, and combinations thereof, in a total amount of amino acids up to about 6% (w/w);
i. a pH adjusting agent selected from the group consisting of tromethamine and hydrochloric acid, and combinations thereof, such that the ophthalmic pharmaceutical formulation pH is at a level in the range from about 6.8 to about 7.8; and
j. water;
wherein the ophthalmic pharmaceutical formulation is preservative-free.

2. An ophthalmic pharmaceutical formulation, comprising:
a. a demulcent comprising povidone with a concentration in the range of between about 1% and about 3% (w/w);
b. a surfactant selected from the group consisting of polyoxyl 40 hydrogenated castor oil at a concentration of about 1% (w/w) and polyoxyl 35 castor oil at a concentration of about 4% (w/w) and combinations thereof;
c. perilla seed oil at a concentration of about 0.15% (w/w);
d. hyaluronic acid or a salt thereof at a concentration of about 0.1% (w/w);
e. one or more antioxidants selected from the group consisting of ascorbic acid or salts thereof, ascorbyl palmitate, Vitamin E, tocopherol, ferulic acid, and trisodium citrate, and combinations thereof;
f. a tonicity agent selected from the group consisting of mannitol, sorbitol, and dextrose, and combinations thereof, in a total amount of up to about 5% (w/w);
g. carbomer copolymer type B at a concentration of about 0.005% (w/w);
h. one or more amino acids selected from the group consisting of glutamic acid, serine, phenylalanine, aspartic acid, threonine, leucine, lysine, and isoleucine, and combinations thereof, in a total amount of amino acids up to about 6% (w/w);
i. a pH adjusting agent selected from the group consisting of tromethamine and hydrochloric acid, and combinations thereof, such that the ophthalmic pharmaceutical formulation pH is at a level in the range from about 6.8 to about 7.8; and
j. water;
wherein the ophthalmic pharmaceutical formulation is preservative-free.

3. An ophthalmic pharmaceutical formulation, comprising:
a. a demulcent selected from the group consisting of povidone at a concentration of about 1.25% (w/w) and povidone at a concentration of about 1.5% (w/w);
b. a surfactant selected from the group consisting of polyoxyl 40 hydrogenated castor oil at a concentration of about 1% (w/w) and polyoxyl 35 castor oil at a concentration of about 4% (w/w), and the surfactant further comprising poloxamer 407 at a concentration of about 2% (w/w) and carbomer copolymer type B at a concentration of about 0.005% (w/w);
c. anchovy oil at a concentration of about 0.15% (w/w);
d. hyaluronic acid or a salt thereof;
e. a tonicity agent selected from the group consisting of mannitol, sorbitol, and dextrose, and combinations thereof, in a total amount of up to about 5% (w/w);
f. tocopherol at a concentration of about 0.002% (w/w), ascorbic acid at a concentration of about 0.1% (w/w), trisodium citrate at a concentration up to about 3% (w/w), and ferulic acid at a concentration of about 0.02% (w/w);
g. one or more amino acids selected from the group consisting of glutamic acid, serine, phenylalanine, aspartic acid, threonine, leucine, lysine, and isoleucine, and combinations thereof, in a total amount of amino acids up to about 6% (w/w);
h. a pH adjusting agent selected from the group consisting of tromethamine and hydrochloric acid, and combinations thereof, such that the ophthalmic pharmaceutical formulation pH is at a level in the range from about 6.8 to about 7.8; and
i. water;
wherein the ophthalmic pharmaceutical formulation is preservative-free.

4. An ophthalmic pharmaceutical formulation, comprising:
a. a demulcent selected from the group consisting of povidone at a concentration of about 1.25% (w/w) and povidone at a concentration of about 1.5% (w/w);
b. a surfactant selected from the group consisting of polyoxyl 40 hydrogenated castor oil at a concentration of about 1% (w/w) and polyoxyl 35 castor oil at a concentration of about 4% (w/w), and the surfactant further comprising poloxamer 407 at a concentration of about 2% (w/w) and carbomer copolymer type B at a concentration of about 0.005% (w/w);
c. chia seed oil at a concentration of about 0.15% (w/w);
d. hyaluronic acid or a salt thereof;
e. a tonicity agent selected from the group consisting of mannitol, sorbitol, and dextrose, and combinations thereof, in a total amount of up to about 5% (w/w);
f. tocopherol at a concentration of about 0.002% (w/w), ascorbic acid at a concentration of about 0.1% (w/w), trisodium citrate at a concentration up to about 3% (w/w), and ferulic acid at a concentration of about 0.02% (w/w);
g. one or more amino acids selected from the group consisting of glutamic acid, serine, phenylalanine, aspartic acid, threonine, leucine, lysine, and isoleucine, and combinations thereof, in a total amount of amino acids up to about 6% (w/w);
h. a pH adjusting agent selected from the group consisting of tromethamine and hydrochloric acid, and combinations thereof, such that the ophthalmic pharmaceutical formulation pH is at a level in the range from about 6.8 to about 7.8; and i. water;
wherein the ophthalmic pharmaceutical formulation is preservative-free.

5. An ophthalmic pharmaceutical formulation, comprising:
   a. a demulcent selected from the group consisting of povidone at a concentration of about 1.25% (w/w) and povidone at a concentration of about 1.5% (w/w);
   b. a surfactant selected from the group consisting of polyoxyl 40 hydrogenated castor oil at a concentration of about 1% (w/w) and polyoxyl 35 castor oil at a concentration of about 4% (w/w), and the surfactant further comprising poloxamer 407 at a concentration of about 2% (w/w) and carbomer copolymer type B at a concentration of about 0.005% (w/w);
   c. pecan nut oil at a concentration of about 0.15% (w/w);
   d. hyaluronic acid or a salt thereof;
   e. a tonicity agent selected from the group consisting of mannitol, sorbitol, and dextrose, and combinations thereof, in a total amount of up to about 5% (w/w);
   f. tocopherol at a concentration of about 0.002% (w/w), ascorbic acid at a concentration of about 0.1% (w/w), trisodium citrate at a concentration up to about 3% (w/w), and ferulic acid at a concentration of about 0.02% (w/w);
   g. one or more amino acids selected from the group consisting of glutamic acid, serine, phenylalanine, aspartic acid, threonine, leucine, lysine, and isoleucine, and combinations thereof, in a total amount of amino acids up to about 6% (w/w);
   h. a pH adjusting agent selected from the group consisting of tromethamine and hydrochloric acid, and combinations thereof, such that the ophthalmic pharmaceutical formulation pH is at a level in the range from about 6.8 to about 7.8; and
   i. water;
   wherein the ophthalmic pharmaceutical formulation is preservative-free.

6. An ophthalmic pharmaceutical formulation, comprising:
   a. a demulcent selected from the group consisting of povidone at a concentration of about 1.25% (w/w) and povidone at a concentration of about 1.5% (w/w);
   b. a surfactant selected from the group consisting of polyoxyl 40 hydrogenated castor oil at a concentration of about 1% (w/w) and polyoxyl 35 castor oil at a concentration of about 4% (w/w), and the surfactant further comprising poloxamer 407 at a concentration of about 2% (w/w) and carbomer copolymer type B at a concentration of about 0.005% (w/w);
   c. perilla seed oil at a concentration of about 0.15% (w/w);
   d. hyaluronic acid or a salt thereof;
   e. a tonicity agent selected from the group consisting of mannitol, sorbitol, and dextrose, and combinations thereof, in a total amount of up to about 5% (w/w);
   f. tocopherol at a concentration of about 0.002% (w/w), ascorbic acid at a concentration of about 0.1% (w/w), trisodium citrate at a concentration up to about 3% (w/w), and ferulic acid at a concentration of about 0.02% (w/w);
   g. one or more amino acids selected from the group consisting of glutamic acid, serine, phenylalanine, aspartic acid, threonine, leucine, lysine, and isoleucine, and combinations thereof, in a total amount of amino acids up to about 6% (w/w);
   h. a pH adjusting agent selected from the group consisting of tromethamine and hydrochloric acid, and combinations thereof, such that the ophthalmic pharmaceutical formulation pH is at a level in the range from about 6.8 to about 7.8; and
   i. water;
   wherein the ophthalmic pharmaceutical formulation is preservative-free.

7. An ophthalmic pharmaceutical formulation, comprising:
   a. castor oil at a concentration of about 0.15% (w/w);
   b. polyoxyl 35 castor oil at a concentration of about 4% (w/w);
   c. poloxamer 407 at a concentration of about 2% (w/w);
   d. carbomer copolymer type B at a concentration of about 0.005% (w/w);
   e. povidone at a concentration of about 1.25% (w/w);
   f. sodium hyaluronate at a concentration of about 0.1% (w/w);
   g. sorbitol at a concentration of about 4.5%; and
   h. water.

8. An ophthalmic pharmaceutical formulation, comprising:
   a. tocopherol at a concentration of about 0.002% (w/w);
   b. castor oil at a concentration of about 0.15% (w/w);
   c. polyoxyl 35 castor oil at a concentration of about 4% (w/w);
   d. poloxamer 407 at a concentration of about 2% (w/w);
   e. carbomer copolymer type B at a concentration of about 0.005% (w/w);
   f. povidone at a concentration of about 1.25%;
   g. ascorbic acid at a concentration of about 0.1%;
   h. trisodium citrate at a concentration of about 0.45%;
   i. sodium hyaluronate at a concentration of about 0.1% (w/w);
   j. sorbitol at a concentration of about 3.3% (w/w); and
   k. water.

9. An ophthalmic pharmaceutical formulation, comprising:
   a. castor oil at a concentration of about 0.15% (w/w);
   b. polyoxyl 40 castor oil at a concentration of about 1% (w/w);
   c. poloxamer 407 at a concentration of about 2% (w/w);
   d. carbomer copolymer type B at a concentration of about 0.005% (w/w);
   e. povidone at a concentration of about 1.25% (w/w);
   f. ascorbic acid at a concentration of about 0.03% (w/w);
   g. trisodium citrate at a concentration of about 0.55% (w/w);
   h. sodium hyaluronate at a concentration of about 0.1% (w/w);
   i. glutamic acid at a concentration of about 0.084% (w/w);
   j. serine at a concentration of about 0.061% (w/w);
   k. phenylalanine at a concentration of about 0.037% (w/w);
   l. aspartic acid at a concentration of about 0.03% (w/w);
   m. threonine at a concentration of about 0.028% (w/w);
   n. leucine at a concentration of about 0.022% (w/w);
   o. lysine at a concentration of about 0.14% (w/w);
   p. dextrose at a concentration of about 3% (w/w); and
   q. water.

10. An ophthalmic pharmaceutical formulation, comprising:
   a. castor oil at a concentration of about 0.15% (w/w);
   b. polyoxyl 40 castor oil at a concentration of about 1% (w/w);
   c. poloxamer 407 at a concentration of about 2% (w/w);
   d. carbomer copolymer type B at a concentration of about 0.005% (w/w);
   e. povidone at a concentration of about 1.25% (w/w);
   f. ascorbic acid at a concentration of about 0.03% (w/w);

g. trisodium citrate at a concentration of about 0.55% (w/w);
h. sodium hyaluronate at a concentration of about 0.1% (w/w);
i. glutamic acid at a concentration of about 0.084% (w/w);
j. serine at a concentration of about 0.061% (w/w);
k. phenylalanine at a concentration of about 0.037% (w/w);
l. aspartic acid at a concentration of about 0.03% (w/w);
m. threonine at a concentration of about 0.028% (w/w);
n. leucine at a concentration of about 0.022% (w/w);
o. lysine at a concentration of about 0.14% (w/w);
p. trehalose at a concentration of about 3% (w/w);
q. dextrose at a concentration of about 1% (w/w); and
r. water.

11. The ophthalmic pharmaceutical formulation of claim 1, further comprising lanolin.

12. The ophthalmic pharmaceutical formulation of claim 2, further comprising lanolin.

13. The ophthalmic pharmaceutical formulation of claim 3, further comprising lanolin.

14. The ophthalmic pharmaceutical formulation of claim 4, further comprising lanolin.

15. The ophthalmic pharmaceutical formulation of claim 5, further comprising lanolin.

16. The ophthalmic pharmaceutical formulation of claim 6, further comprising lanolin.

17. The ophthalmic pharmaceutical formulation of claim 7, further comprising lanolin.

18. The ophthalmic pharmaceutical formulation of claim 8, further comprising lanolin.

19. The ophthalmic pharmaceutical formulation of claim 9, further comprising lanolin.

20. The ophthalmic pharmaceutical formulation of claim 10, further comprising lanolin.

* * * * *